United States Patent

Hamanaka

Patent Number: 6,001,860

Date of Patent: Dec. 14, 1999

[54] N-ARYL AND N-HETEROARYLUREA DERIVATIVES AS INHIBITORS OF ACYL COENZYME A: CHOLESTEROL ACYL TRANSFERASE (ACAT)

[75] Inventor: Ernest S. Hamanaka, Gales Ferry, Conn.

[73] Assignee: Pfizer Inc., New York, N.Y.

[21] Appl. No.: 08/343,557

[22] PCT Filed: Apr. 20, 1993

[86] PCT No.: PCT/US93/03539

§ 371 Date: Jan. 17, 1995

§ 102(e) Date: Jan. 17, 1995

[87] PCT Pub. No.: WO93/24458

PCT Pub. Date: Dec. 9, 1993

Related U.S. Application Data

[63] Continuation-in-part of application No. 07/890,050, May 28, 1992, abandoned.

[51] Int. Cl.[6] .......................... A61K 31/44; C07D 213/75
[52] U.S. Cl. ...................... 514/353; 514/235.5; 514/318; 514/343; 514/349; 544/131; 546/194; 546/276.4; 546/285; 546/291; 546/293; 546/306
[58] Field of Search ..................................... 514/349, 352, 514/235.5, 318, 343; 546/288, 289, 309, 194, 276.4, 285, 291, 293, 306; 544/131

[56] References Cited

U.S. PATENT DOCUMENTS

| | | | |
|---|---|---|---|
| 3,426,031 | 2/1969 | Fischback | 260/295 |
| 4,623,662 | 11/1986 | De Vries | 514/596 |
| 4,716,175 | 12/1987 | Hoefle et al. | 514/357 |
| 4,743,605 | 5/1988 | Hoefle et al. | 514/269 |
| 4,994,465 | 2/1991 | Trivedi | 514/256 |

FOREIGN PATENT DOCUMENTS

| | | |
|---|---|---|
| 0242610 | 10/1987 | European Pat. Off. . |
| 0252524 | 1/1988 | European Pat. Off. . |
| 0384320 | 8/1990 | European Pat. Off. . |
| 0399422 | 11/1990 | European Pat. Off. . |
| 0245687 | 2/1991 | European Pat. Off. . |
| 0297610 | 3/1991 | European Pat. Off. . |
| 0418071 | 3/1991 | European Pat. Off. . |
| 0447116 | 9/1991 | European Pat. Off. . |
| 0477778 | 4/1992 | European Pat. Off. . |
| 0293880 | 8/1992 | European Pat. Off. . |
| 0506532 | 9/1992 | European Pat. Off. . |
| 0335374 | 6/1993 | European Pat. Off. . |
| 0335375 | 6/1993 | European Pat. Off. . |
| 0386487 | 1/1994 | European Pat. Off. . |
| 0439059 | 8/1994 | European Pat. Off. . |
| 0415123 | 12/1994 | European Pat. Off. . |
| 0421456 | 12/1994 | European Pat. Off. . |
| 0512570 | 10/1995 | European Pat. Off. . |
| WO9015048 | 12/1990 | WIPO . |
| WO9104027 | 4/1991 | WIPO . |
| WO9113871 | 9/1991 | WIPO . |
| WO9324458 | 12/1993 | WIPO . |

OTHER PUBLICATIONS

Teiji Kimura, et al., J. Med. Chem. 1993, vol. 36 pp. 1630–1640, "Structure—Activity Relationship of N–[2–(Dimethylamino)–6–[3–(5–methyl–4–phenyl–1H–imidazol–1–yl)propoxy] phenyl–N'–pentylurea and Analogues. Novel Potent Inbititors oc Acyl–CoA:Cholesterol O–Acyltransferase with Antiatherosclerotic Activity".

Teiji Kimura, et al, J. Med. Chem. 1993, vol. 36 pp. 1641–1653, "Structure–Activity Relationship of a Series of Phenylureas Linked to 4–Phenylimidazole. Novel Potent Inhibitors of Acyl–CoA:Cholesterol O–Acyltransferase with Antiatherosclerotic Activity. 2".

*Primary Examiner*—Richard L. Raymond
*Attorney, Agent, or Firm*—Peter C. Richardson; Gregg C. Benson; A. Dean Olson

[57] ABSTRACT

A compound of the formula

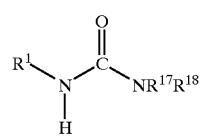

and the pharmaceutically acceptable salts thereof, wherein $R^{17}$, $R^{18}$ and $R^1$ are as defined below. The compounds of formula I are inhibitors of acyl coenzyme A: cholesterol acyltransferase (ACAT) and are useful as hypolipidemic and antiatherosclerosis agents.

5 Claims, No Drawings

N-ARYL AND N-HETEROARYLUREA DERIVATIVES AS INHIBITORS OF ACYL COENZYME A: CHOLESTEROL ACYL TRANSFERASE (ACAT)

This application is a 371 of PCT/US93/03539, filed Apr. 20, 1993 which is a CIP of U.S. application Ser. No. 07/890,050, filed May 28, 1992, now abandoned.

BACKGROUND OF THE INVENTION

The present invention relates to new N-aryl and N-heteroarylurea derivatives, pharmaceutical compositions comprising such compounds, and the use of such compounds to inhibit intestinal absorption of cholesterol, lower serum cholesterol and reverse the development of atherosclerosis. The compounds are inhibitors of acyl coenzyme A: cholesterol acyltransferase (ACAT).

Cholesterol that is consumed in the diet (dietary cholesterol) is absorbed as free cholesterol by the mucosal cells of the small intestine. It is then esterified by the enzyme ACAT, packaged into particles known as chylomicrons, and released into the bloodstream. Chylomicrons are particles into which dietary cholesterol is packaged and transported in the bloodstream. By inhibiting the action of ACAT, the compounds of this invention prevent intestinal absorption of dietary cholesterol and thus lower serum cholesterol levels. They are therefore useful in preventing atherosclerosis, heart attacks and strokes.

By inhibiting the action of ACAT, the compounds of the present invention also enable cholesterol to be removed from the walls of blood vessels. This activity renders such compounds useful in slowing or reversing the development of atherosclerosis as well as in preventing heart attacks and strokes.

Other inhibitors of ACAT are referred to in U.S. Pat. Nos. 4,994,465, 4,716,175 and 4,743,605 (a divisional of the '175 patent) and in the European Patent Applications having publication numbers 0 242 610, 0 245 687, 0 252 524, 0 293 880, 0 297 610, 0 335 374, 0 335 375, 0 386 487, 0 399 422, 0 415 123, 0 421 456 and 0 439 059. Additional ACAT inhibitors are described in PCT publications WO 9015048 and WO 91/04027. Certain ureas and thioureas as antiatherosclerosis agents are referred to in U.S. Pat. No. 4,623,662.

SUMMARY OF THE INVENTION

The present invention relates to compounds of the formula

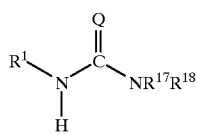

I wherein Q is oxygen or sulfur $R^{17}$ is —$(CH_2)_n$—$(CR^{19}R^{20})_z(CH_2)_r$—Ar  XXXVIII wherein n is 0 or an integer from 1 to 3;

z is 0 or 1;

and r is 0 or an integer from 1 to 4;

$R^{19}$ and $R^{20}$ are independently selected from hydrogen, optionally halogenated $(C_1-C_{12})$ alkyl, optionally substituted aryl-$(C_1-C_5)$ alkyl, $(C_3-C_8)$ cycloalkyl-$(C_1-C_5)$alkyl and Ar; or $R^{19}$ and $R^{20}$ and the carbon to which they are attached form a $(C_5-C_7)$ cycloalkyl ring or a benzene-fused $(C_5-C_7)$ cyclo-alkyl or -heteroalkyl ring; with the proviso that $R^{19}$ and $R^{20}$ cannot both be hydrogen;

Ar is selected from the group consisting of

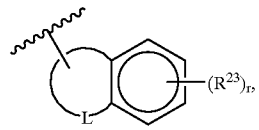

XXX

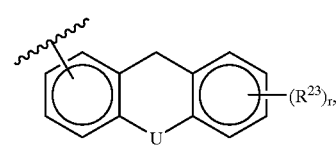

XXXI

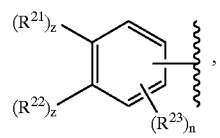

XXXII

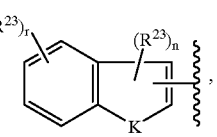

XXXIII

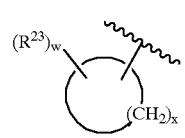

XXXIV and

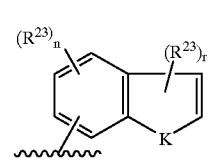

XXXV wherein U is J, a direct bond —CH=CH— or —$CH_2CH_2$—;

z, n and r are as defined above; x is an integer from 3 to 10 and w is 0 or an integer from 1 to x-1.

$R^{21}$, $R^{22}$ and each $R^{23}$ is independently selected from the group consisting of optionally halogenated $(C_1-C_6)$ alkyl, optionally halogenated $(C_1-C_6)$alkoxy, optionally halogenated $(C_1-C_6)$alkylthio, phenyl and halogen; wherein the alkyl groups in said alkyl, alkoxy and althylthio groups may be straight chained or if comprising three or more carbons may be branched, cyclic or a combination of cyclic and branched or straight chained moieties;

or $R^{21}$ and $R^{22}$ together form a group of the formula

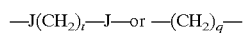

wherein J is oxygen or sulfur;

t is an integer from 1 to 3;

and q is an integer from 3 to 5;

K is J— or —CH=CH—;

L is —(CH$_2$)$_u$ or —(CH$_2$)$_v$J—;

wherein J is as defined above;

u is an integer 3 to 5;

and v is 3 or 4;

R$^{18}$ is hydrogen, optionally substituted (C$_1$–C$_8$)alkyl, optionally substituted (C$_3$–C$_8$)cycloalkyl, aryl or optionally substituted aryl-(C$_1$–C$_4$)alkyl with the proviso that R$^{18}$ is hydrogen if any one of n, z or r in formula XXXVIII is not 0;

R$^1$ is selected from the group consisting of

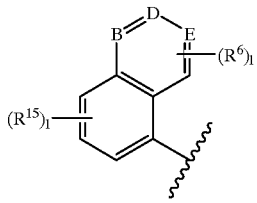

XXIV

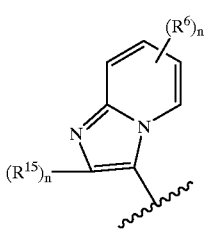

XXV or

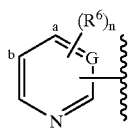

XXVI wherein m is as defined above;

n is 0 or 1.

Each I is independently selected from 0 to 3;

Each R$^6$ and R$^{15}$ is independently selected from the group consisting of halogen, (C$_1$–C$_6$)alkyl, (C$_1$–C$_6$) haloalkyl, optionally halogenated (C$_1$–C$_6$) alkoxy, optionally halogenated (C$_1$–C$_6$) alkylthio, (C$^5$–C$^7$) cycloalkylthio, phenyl (C$_1$–C$_6$)alkylthio, substituted phenylthio, heteroarylthio, heteroaryloxy, (C$_1$–C$_6$) alkylsulfinyl, (C$_1$–C$_6$) alkylsulfonyl, (C$_5$–C$_7$) cycloalkylsulfinyl, (C$_5$–C$_7$) cycloalkylsulfonyl, phenyl (C$_1$–C$_6$) alkylsulfinyl, phenyl (C$_1$–C$_5$) alkylsulfonyl, substituted phenylsulfinyl, substituted phenylsulfonyl, heteroarylsulfinyl, heteroarylsulfonyl, and NR$^{10}$R$^{11}$, wherein R$^{10}$ and R$^{11}$ are the same or different and are selected from the group consisting of hydrogen, (C$_1$–C$_6$) alkyl, phenyl, substituted phenyl, (C$_1$–C$_6$) acyl, aroyl, and substituted aroyl, wherein said substituted phenyl and substituted aroyl groups are substituted with one or more substituents independently selected from the group consisting of (C$_1$–C$_6$) alkyl, (C$_1$–C$_6$) alkoxy, (C$_1$–C$_6$) alkylthio, halogen and trifluoromethyl, or R$^{10}$ and R$^{11}$, together with the nitrogen to which they are attached, form a piperidine, pyrrolidine or morpholine ring; and B, D, E and G are selected from the group consisting of nitrogen and carbon, with the proviso that one or more of B, D and E is nitrogen, and with the proviso that when G is nitrogen, the group XVI is attached to the nitrogen of formula I at the 4 or 5 position of the pyrimidine ring (designated by a and b) wherein any of said nitrogens may be oxidized;

or R$^1$ is

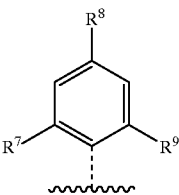

XXVII wherein R$^7$, R$^9$ and R$^9$ may be the same or different and each is independently selected from the group consisting of optionally halogenated (C$_1$–C$_5$)alkoxy, optionally halogenated (C$_1$–C$_5$)alkylthio, optionally halogenated (C$_1$–C$_5$)alkyl and halogen; with the proviso that when R$^1$ is a group of the formula XXVII Ar is a group of formula XXXII, XXXIII or XXXV and when Ar is XXXII R$^{19}$ or R$^{20}$ is not alkyl and r in formula XXXVIII is 0; or a pharmaceutically acceptable salt of said compound.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

Unless otherwise indicated, the term "one or more substituents", as used herein, refers to from one to the maximum number of substituents possible based on the number of available bonding sites.

The term "one or more carbons of said non-aromatic ring", as used herein, refers to from one to all of the carbon atoms that are part of the non-aromatic ring of any of the aryl-fused or heteroaryl-fused systems described above, and not part of the aromatic ring of said aryl-fused system.

The term "one or more carbons of said aromatic ring", as used herein, refers to from one to all of the carbon atoms that are part of the aromatic ring of any of the aryl-fused and heteroaryl-fused systems described above, or are part of both said aromatic and non-aromatic rings of said aryl-fused and heteroaryl-fused system.

The compounds of formula I may have optical centers and therefore may occur in different stereoisomeric configurations. The invention includes all stereoisomers of such compounds of formula I, including mixtures thereof.

The present invention also relates to compounds of the formula

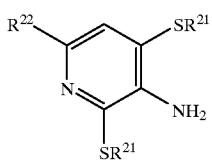

XXVIII wherein R$^{21}$ is (C$_1$–C$_3$) alkyl and R$^{22}$ is hydrogen or (C$_1$–C$_3$) alkyl.

Preferred compounds of formula I are those wherein R$_1$ is 2,4,6-trifluorophenyl, 2,6-diisopropylphenyl, 2,4- difluorophenyl, 6-methoxyquinolin-5-yl, 6-methylquinolin-5-yl, 6-methylthioquinolin-5-yl, 6-methoxyisoquinolin-5-yl, 6-methylthioisoquinolin-5-yl, 6methylthio-8-acetaminoquinolin-5-yl, 4,6-bis(methylthio)pyrimidin-5yl, 4,6-bis(methylthio)-2-methylpyrimidin-5-yl, 2,4-bis(methylthio)pyridin-3-yl, 2,4-bis(methylthio)-6-methylpyridin-3-yl, 2,4-bis(ethylthio)-6-methylpyridin-3-yl, 2,4-bis(methylthio)pyridin-3-yl and 2,4-bis(isopropylthio)-6-methylpyridin-3-yl.

Specific preferred compounds of formula I are:

N-[2,4-Bis(methylthio)-6-methylpyridin-3-yl]-N'-(indan-2-yl)-N'-(4-isopropylbenzyl)urea;

N-[2,4Bis(methylthio)-6-methylpyridin-3-yl]-N'-(2,5-dimethylbenzyl)-N'-(indan-2-yl)urea;

N-[2,4-Bis(methylthio)-6-methylpyridin-3-yl]-N'-(2,4-dimethylbenzyl)-N'-(indan-2-yl)urea;

N-[4,6-Bis(methylthio)-2-methylpyrimidin-5-yl]-N'-(indan-2-yl)-N'-(4-isopropylbenzyl)urea;

N-[4,6-Bis(methylthio)-2-methylpyrimidin-5yl]-N'-(2,4dimethylbenzyl)-N'-(indan-2-yl)urea;

N-(2,5-Dimethylbenzyl)-N-(indan-2-yl)-N'-(6-methylthioquinolin-5yl)urea;

N-[2,4-Bis(methylthio)-6-methylpyridin-3-yl]-N'-(2-chlorobenzyl)-N'-(indan-2-yl)urea;

N-[4,6-Bis(methylthio)-2-methylpyrimidin-5-yl]-N'-(2,5dimethylbenzyl)-N'-(indan-2-yl)urea;

N-[4,6-Bis(methylthio)-2-methylpyrimidin-5-yl]-N'-(indan-2-yl)-N'-[4-(3-methylbutyl)benzyl]urea;

N-[2,4-Bis(methylthio)-6-methylpyridin-3-yl]-N'-(indan-2-yl)-N'-[4-(3-methylbutyl)benzyl]urea;

N-[2,4-Bis(methylthio)-6-methylpyridin-3-yl]-N'-(indan-1-yl)-N'-(naphth-1-ylmethyl)urea;

N-[2,4-Bis(methylthio)-6-methylpyridin-3-yl]-N'-(indan-1-yl)-N'-(naphth-2-ylmethyl)urea;

N-[2,4-Bis(methylthio)-6-methylpyridin-3-yl]-N'-(indan-1-yl)-N'-(4-t-butylbenzyl)urea;

N-[2,4-Bis(methylthio)-6-methylpyridin-3-yl]-N'-(indan-1-yl)-N'-(4-phenylbenzyl)urea;

N-[2,4-Bis(methylthio)-6-methylpyridin-3-yl]-N'-(indan-2-yl)-N'-(naphth-1-ylmethyl)urea;

N-[2,4-Bis(methylthio)-6-methylpyridin-3-yl]-N'-(indan-2-yl)-N'-(naphth-2-ylmethyl)urea;

N-[2,4-Bis(ethylthio)-6methylpyridin-3-yl]-N'-cycloheptyl-N'-(4-phenylbenzyl)urea;

N-[2,4-Bis(ethylthio)-6-methylpyridin-3-yl]-N'-cycloheptyl-N'-(fluoren-2-yl-methyl)urea;

N-[2,4-Bis(ethylthio)-6-methylpyridin-3-yl]-N'-cycloheptyl-N'-(naphth-2-ylmethyl)urea;

N-[2,4-Bis(ethylthio)-6-methylpyridin-3-yl]-N'-heptyl-N'-[naphth-2-ylmethyl]urea;

N-[2,4-Bis(ethylthio)-6-methylpyridin-3-yl]-N'-heptyl-N'-(2,4,6-trimethylbenzyl)urea;

N-[2,4-Bis(methylthio)-6-methylpyridin-3-yl]-N'-cycloheptyl-N'(4-phenylbenzyl)urea;

N-[2,4-Bis(methylthio)-6-methylpyridin-3-yl]-N'-cycloheptyl-N'-(fluoren-2-ylmethyl)urea;

N-[2,4-Bis(ethylthio)-6-methylpyridin-3-yl]-N'-(4-isopropylbenzyl)-N'-(1,2,3,4-tetrahydro-naphth-2-yl)urea;

N-[2,4-Bis(ethylthio)-6-methylpyridin-3-yl]-N'-heptyl-N'-(3methylbenzo[b]thiophen-2-ylmethyl)urea;

N-[2,4-Bis(ethylthio)-6-methylpyridin-3-yl]-N'-(1,2,3,4-tetrahydronaphth-2-yl)-N'-(2,4,6-trimethylbenzyl)urea;

N-[2,4-Bis(methylthio)-6-methylpyridin-3-yl]-N'-cycloheptyl-N'-(naphth-2-ylmethyl)urea;

N-[2,4-Bis(ethylthio)-6-methylpyridin-3-yl]-N'-(indan-2-yl)-N'-(4-isopropylbenzyl)urea;

N-[2,4-Bis(ethylthio)-6-methylpyridin-3-yl] -N'-(2,4-dimethylbenzyl)-N'-(indan-2-yl)urea;

N-[2,4-Bis(methylthio)-6-methylpyridin-3-yl]-N'-(4-isopropylbenzyl)-N'-(6,7,8,9-tetrahydro-5H-benzocyclohepten-7-yl)urea;

N-[2,4-Bis(ethylthio)-6-methylpyridin-3-yl]-N'-(indan-2-yl)-N'-(2,4,6-trimethylbenzyl)urea;

N-[2,4-Bis(methylthio)-6-methylpyridin-3-yl]-N'-(indan-2-yl)-N'-(2,4,6-trimethylbenzyl)urea;

N-[2,4-Bis(methylthio)-6-methylpyridin-3-yl]-N'-(2,3-dichlorobenzyl)-N'-(indan-2-yl)urea:

N-[2,4-Bis(methylthio)-6-methylpyridin-3-yl]-N'-[2,2-diphenylethyl]urea;

N-[2,2-Diphenylethyl]-N'-(6-methylthioquinolin-5-yl)urea;

N-[4,6-Bis(methylthio)-2-methylpyrimidin-5-yl]-N'-(2,2-diphenylethyl)urea;

N-[4,6-Bis(methylthio)pyrimidin-5-yl]-N'-(2,2-diphenylethyl)urea;

N-[2,4-Bis(methylthio)-6-methylpyridin-3-yl]-N'-[(1-phenylcyclopentyl)methyl]urea;

N-(6-Methylthioquinolin-5-yl)-N'-[(1-phenylcyclopentyl)methyl]urea;

N-[2,4-Bis(methylthio)-6-methylpyridin-3-yl]-N'-[{1-(4-methylphenyl)cyclopentyl}methyl]urea;

N-[{1-(4-Methylphenyl)cyclopentyl}methyl]-N'-(6-methylthioquinolin-5-yl)urea;

N-(6-Methylthioquinolin-5-yl)-N'-[(1-phenylcyclohexyl)methyl]urea;

N-[2,4-Bis(methylthio)-methylpyridin-3-yl]-N'-[(1-phenylcyclohexyl)methyl]urea;

N-[{1-(4-Methylphenyl)cyclohexyl}methyl]-N'-(6-methylthioquinolin-5-yl)urea;

N-[4,6-Bis(methylthio)-2-methylpyrimidin-5-yl]-N'-[{1-(4-methylphenyl)cyclohexyl}methyl]urea;

N-[2,4-Bis(methylthio)-6-methylpyridin-3-yl]-N'-[{1-(4-methylphenyl)cyclohexyl}methyl]urea;

N-2,4-Bis(methylthio)-6-methylpyridin-3-yl]-N'-[(2-ethyl-2-phenyl)butyl]urea;

N-[2,4-Bis(isopropylthio)-6-methylpyridin-3-yl]-N'-[(2-ethyl-2-phenyl)butyl]urea;

N-[2,4-Bis(methylthio)-6-methylpyridin-3-yl-N'-[(2-ethyl-2-{2-methylphenyl})butyl]urea;

N-[2,4-Bis(methylthio)-6-methylpyridin-3-yl-N'-[(2-phenyl-2-propyl)pentyl]urea;

N-[2,4-Bis(methylthio)-6-methylpyridin-3-yl-N'-[(2-{2-methylphenyl}-2-propyl)pentyl]urea;

N-[2,4-Bis(methylthio)-6-methylpyridin-3-yl-N'-[(2-{2-methylphenyl}-2-butyl)hexyl]urea;

N-[2,4-Bis(methylthio)-6-methylpyridin-3-yl-N'-[(2-{2,5-dimethoxyphenyl}-2-propyl)pentyl]urea;

N-[2,4-Bis(methylthio)-6-methylpyridin-3-yl-N'-[(2-{2,3-dimethoxyphenyl}-2-propyl)pentyl]urea;

N-[2,4-Bis(methylthio)-6-methylpyridin-3-yl-N'-[(2-{2,5-dimethylphenyl}-2-propyl)pentyl]urea;

N-[2,4-Bis(methylthio)-6-methylpyridin-3-yl]-N'-[2-(2-methylphenyl)hexyl]urea;

N-[2-(2-Methylphenyl)hexyl]-N'-[6-methylthioquinolin-5-yl]urea;

N-[2,4-Bis (methylthio)-6-methylpyridin-3-yl]-N'-[2-(4-methylphenyl)heptyl]urea;

N-[2-(4-Methylphenyl)heptyl]-N'-(6-methylthioquinolin-5-yl)urea;

N-[2,4-Bis(methylthio)-6-methylpyridin-3-yl]-N'-(2-(3-methylphenyl)heptyl]urea;

N-[2-(3-Methylphenyl)heptyl]-N'-(6-methylthioquinolin-5-yl)urea;

N-[2-(3-Methylphenyl)heptyl]-N'-(6-methoxyquinolin-5-yl)urea;

N-[2,4-Bis(methylthio)-methylpyridin-3-yl]-N'-[2-(2,5-dimethylphenyl)hexyl]urea;

N-[2-(2,5-Dimethylphenyl)hexyl]-N'-(6-methylthioquinolin-5-yl)urea;

N-[2-(2,5-Dimethylphenyl)hexyl]-N'-(6-methoxyquinolin-5-yl)urea;

N-[2,4-Bis(methylthio)-6-methylpyridin-3-yl]-N'-[2-(2,5dimethylphenyl)heptyl]urea;

N-[2,4-Bis(methylthio)-6-methylpyridin-3-yl]-N'-[2-(2,4-dimethylphenyl)hexyl]urea;

N-[2,4-Bis(methylthio)-6-methylpyridin-3-yl]-N'-[2-(3-methylphenyl)hexyl]urea;

N-[2,4-Bis(methylthio)-6-methylpyridin-3-yl]-N'-[2-(2,4-dimethylphenyl)heptyl)urea;

N-[2,4-Bis(methylthio)-6-methylpyridin-3-yl]-N'-[2-(naphth-1-yl)heptyl]urea;

N-[2,4-Bis(methylthio)-6-methylpyridin-3-yl]-N'-[2-(naphth-2-yl)hexyl]urea;

N-[2,4-Bis(methylthio)-6-methylpyridin-3-yl]-N'-[2-(naphth-1-yl)hexyl]urea;

N-(6-Methylthioquinolin-5-yl)-N'-[2-(naphth-1-yl)hexyl]urea;

N-[2,4-Bis(methylthio)-6-methylpyridin-3-yl]-N'-[2-(2,3-dimethoxyphenyl)heptyl)-urea;

N-[2-(2,3-Dimethoxyphenyl)heptyl]-N'-(6-methylthioquinolin-5-yl)urea;

N-[2,4-Bis(methylthio)-6-methylpyridin-3-yl]-N'-[2-(3-methylphenyl)octyl]urea;

N-[2-(3-Methylphenyl)octyl]-N'-(6-methoxyquinolin-5-yl]urea;

N-[2-(3-Methylphenyl)octyl]-N'-(6-methylthioquinolin-5-yl]urea;

N-[2-(Naphth-1-yl)heptyl]-N'-(6-methoxyquinolin-5-yl)urea;

N-[2-(Naphth-1-yl)heptyl]-N'-(6-methylthioquinolin-5-yl)urea;

N-[2-(2,4-Dimethylphenyl)heptyl]-N'-(6-methylthioquinolin-5-yl)urea;

N-[2-(2,4-Dimethylphenyl)heptyl]-N'-(6-methoxyquinolin-5-yl)urea;

N-[2,4-Bis(methylthio)-6-methylpyridin-3-yl]-N'2-(3,4,5-trimethoxyphenyl)heptyl]urea;

N-[2,4-Bis(methylthio)-6-methylpyridin-3-yl]-N'-[2-(2,5-dimethyl-4-methoxyphenyl)heptyl]urea;

N-[2,4-Bis(methylthio)-6-methylpyridin-3-yl]-N'-[2-(2,5-dimethoxyphenyl)-phenylbutyl]urea;

N-[2-(2,5-Dimethoxyphenyl)heptyl]-N'-(6-methylthioquinolin-5-yl) urea;

N-[2-(2,5-Dimethoxyphenyl)heptyl-N'-(6-methoxyquinolin-5-yl)urea;

N-[2,4-Bis(methylthio)-6-methylpyridin-3-yl]-N'-[2-(3,5-dimethoxyphenyl)heptyl]urea;

N-[2,4-Bis(methylthio)-6-methylpyridin-3-yl]-N'-[2-(2,5-dimethoxyphenyl)octyl]urea;

N-[2,4-Bis(methylthio)-6-methylpyridin-3-yl]-N'-2-[2-(3-methylphenyl)-6,6,6-trifluorohexyl]urea;

N-[2-(3-Methylphenyl)heptyl]-N'-(6-pentylthioquinolin-5-yl)urea;

N-[2,4-Bis(methylthio)-6-methylpyridin-3-yl]-N'-{2-(5-chlorobenzo[b]thiophen-3-yl)heptyl}urea;

N-[2,4-Bis(methylthio)-6-methylpyridin-3-yl]-N'-[2-(3,5-dimethylphenyl)heptyl]urea;

N-[2,4-Bis(methylthio)-6-methylpyridin-3-yl]-N'-[2-(2,5-dimethylphenyl)octyl]urea;

N-[2,4-Bis(methylthio)-6-methylpyridin-3-yl]-N'-[5-methyl-2-{3-methylphenyl}hexyl]urea;

N-[2,4-Bis(methylthio)-6-methylpyridin-3-yl]-N'-[(2-{2,5-dimethylphenyl}-4-phenylbutyl]urea;

N-[2,4-Bis(methylthio)-6-methylpyridin-3-yl]-N'-[2-(2,6-dimethylphenyl)-5-phenylpentyl]urea;

N-[2,4-Bis(methylthio)-6-methylpyridin-3-yl]-N'-[2-(naphth-1-yl)-6-methylheptyl]urea;

N-[2,4-Bis(ethylthio)-6-methylpyridin-3-yl]-N'-[2-(naphth-1-yl)-6-methylheptyl]urea;

N-[2,4-Bis(ethylthio)-6-methylpyridin-3-yl]-N'-[2-(2,5-dimethylphenyl)-6-methylheptyl]urea;

N-[2,4-Bis(ethylthio)-6-methylpyridin-3-yl]-N'-[2-(naphth-1-yl)heptyl]urea;

N-[2,4-Bis(ethylthio)-6-methylpyridin-3-yl]-N'-[2-(2,5-dimethylphenyl)-6-phenylhexyl]urea;

N-[2,4-Bis(ethylthio)-6-methylpyridin-3-yl]-N'-[2-(2,5-dimethylphenyl)heptyl]urea;

N-[2,4-Bis(methylthio)-6-methylpyridin-3-yl]-N'-[2-(2,4,6-trimethylphenyl)octyl]urea;

N-[2,4-Bis(ethylthio)-6-methylpyridin-3-yl]-N'-[2-(2,5-dimethylphenyl)-6,6,6-trifluorohexyl]urea;

N-[2,4-Bis(methylthio)-6-methylpyridin-3-yl]-N'-[2-(5-methylbenzo[b]thiophen-3-yl)heptyl]urea;

N-[2,4-Bis(methylthio)-6-methylpyridin-3-yl]-N'-[2-(2-chlorobenzo[b]thiophen-3-yl)heptyl]urea;

N-[2-(2,5-Dimethylphenyl)heptyl]-N'-[6-methylthioquinolin-5-yl]urea;

N-[2,4-Bis(methylthio)-6-methylpyridin-3-yl]-N'-[2-(2,5-dimethylphenyl)-6-methylheptyl]urea;

N-[2,4-Bis(ethylthio)-6-methylpyridin-3-yl]-N'-[2-(2,5-dimethylphenyl)-5-phenylpentyl]urea;

N-[2,4-Bis(ethylthio)-6-methylpyridin-3-yl]-N'-[2-(2,5-dimethylphenyl)octyl]urea;

N-[2,4-Bis(ethylthio)-6-methylpyridin-3-yl]-N'-[2,5-dimethylphenyl)octyl]urea;

N-[2,4-Bis(ethylthio)-6-methylpyridin-3-yl]-N'-[2,5-dimethylphenyl)-5-methylhexyl]urea;

N-[2,4-Bis(ethylthio)-6-methylpyridin-3-yl]-N'-[2-(2chlorobenzo[b]thiophen-3yl)6-methylheptyl]urea;

N-[2,4-Bis(ethylthio)-6-methylpyridin-3-yl]-N'-[2-(2chlorobenzo[b]thiophen-3-yl)-5-methylhexyl]urea;

N-[2,4-Bis(ethylthio)-6-methylpyridin-3-yl]-N'-[2-(5,6,7,8-tetrahydronaphth-1-yl)heptyl]urea;

N-[2,4-Bis(ethylthio)-6-methylpyridin-3-yl]-N'-[2-(3,5-dimethylphenyl)heptyl]urea;

N-[2,4-Bis(ethylthio)-6-methylpyridin-3-yl]-N'-[2-(2-chlorobenzo[b]thiophen-3-yl)heptyl]urea;

N-[2,4-Bis(ethylthio)-6-methylpyridin-3-yl]-N'-[2-(3,5-dimethylphenyl)octyl]urea;

N-[2,4-Bis(ethylthio)-6-methylpyridin-3-yl]-N'-[2-(2,5-dimethyl-4-methoxyphenyl)heptyl]urea;

N-[2,4-Bis(methylthio)-6-methylpyridin-3-yl]-N'-[2-(5-methylbenzo[b]thiophen-3-yl)heptyl]urea;

N-[2-(2-Chlorobenzo[b]thiophen-3-yl)-5-methylhexyl]-N'-(2,6-diisopropyl)urea;

N-(2,6-Diisopropylphenyl)-N'-[2-(5-methylbenzo[b]thiophen-3-yl-5-methylhexyl]urea;

N-[2-(Benzo[b]thiophen-3-yl)heptyl]-N'-(2,6-diisopropylphenyl)urea;

N-[2-(Benzo[b]thiophen-3-yl)-6-methylheptyl]-N'-(2,6-diisopropylphenyl)urea;

N-[2-(2-Chlorobenzo[b]thiophen-3-yl)-6-methylheptyl]-N'-(2,6-diisopropylphenyl)urea;

N-(2,6-Diisopropylphenyl)-N'-[2-(5-methylbenzo[b]thiophen-3-yl)-6,6,6-trifluorohexyl]urea;

N-[2-(2-Chlorobenzo[b]thiophen-3-yl)-6,6,6-trifluorohexyl]-N'-(2,6-diisopropylphenyl)urea;

N-(2,6-Diisopropylphenyl)-N'-[2-(naphth-2-yl)-6,6,6-trifluorohexyl]urea;

N-[7,7-Difluoro-2-(naphth-1-yl)heptyl]-N'-(2,6-diisopropylphenyl)urea;

N-[7,7-difluoro-2-(2-chlorobenzo[b]thiophen-3-yl)heptyl]-N'-(2,6-diisopropylphenyl)urea;

N-[2-(5-Chlorobenzo [b]thiophen-3-yl)heptyl]-N'-(2,6-diisopropylphenyl)urea;

N-[2-(2-Chlorobenzo[b]thiophen-3-yl)heptyl]-N'-(2,6-diisopropylphenyl)urea;

N-[2-(5-Chlorobenzo[b]thiophen-3-yl)-6,6,6-trifluorohexyl]-N'-(2,6-diisopropylphenyl)urea;

N-(2,6-(Diisopropylphenyl)-N'-[2-(5-methylbenzo[b]thiophen-3-yl)heptyl]urea;

N-[2-(5-Chlorobenzo[b]thiophen-3-yl)-6-methylheptyl]-N'-(2,6-diisopropylphenyl)urea;

N-(2,6-(Diisopropylphenyl))-N'-[2-(2,5-dimethylphenyl)-6,6,6-trifluorohexyl]urea;

N-[7,7-Difluoro-2-(2,5-dimethylphenyl)heptyl]-N'-(2,6-diisopropylphenyl)urea;

N-(2,6-Diisopropylphenyl)-N'-[2-(napth-1-yl)heptyl]urea;

and

N-(2,6-Diisopropylphenyl)-N'-[6-methyl-2-(napth-1-yl)heptyl]urea.

The present invention also relates to all radiolabelled forms of the compounds of the formulae I, II and XXVIII. Such radiolabelled compounds are useful as research and diagnostic tools in metabolism pharmacokinetic studies and in binding assays in both animals and man.

The present invention also relates to a pharmaceutical composition for inhibiting ACAT, inhibiting intestinal absorption of cholesterol, reversing or slowing the development of atherosclerosis, or lowering the concentration of serum cholesterol in a mammal, including a human, comprising an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol, and a pharmaceutically acceptable carrier.

The present invention also relates to a method for inhibiting ACAT, inhibiting intestinal absorption of cholesterol, reversing or slowing the development of atherosclerosis, or lowering the concentration of serum cholesterol in a mammal, including a human, comprising administering to a mammal an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol.

Examples of pharmaceutically acceptable acid addition salts of the compounds of formula I salts are the salts of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

DETAILED DESCRIPTION OF THE INVENTION

The reaction scheme below illustrates the synthesis of certain 5-aminoquinolines and 5-aminoisoquinolines used in the practice of this invention.

Except where otherwise stated, Q, $R^1$, $R^6$, $R^7$, $R^8$, $R^9$, $R^{15}$, $R^{17}$, $R^{18}$, n, m, o, p, A, B, D, E and G in the reaction schemes and discussion that follows are defined as above.

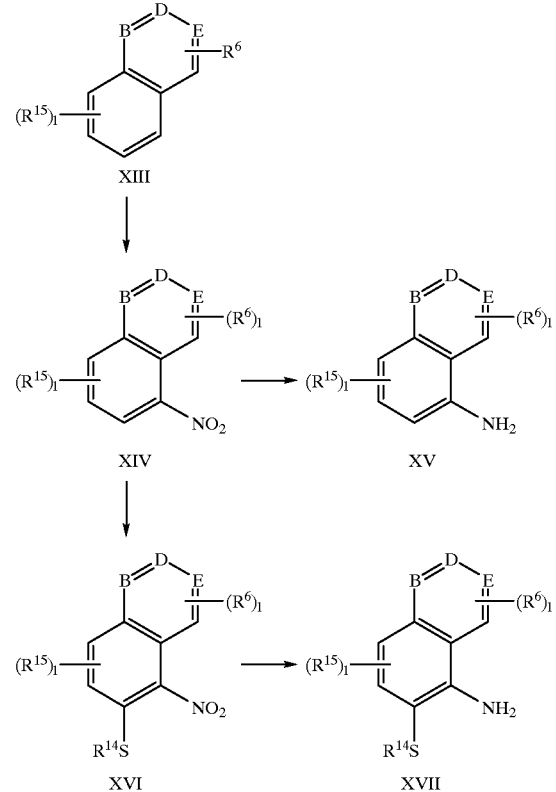

SCHEME 1

The aminopyrimidine and aminopyridine intermediates used in the present invention are known in the literature or may be prepared by methods known in the art from intermediates that are known in the literature or commercially available. References for the preparation of many of the pyrimidine and pyridine intermediates can be found in the monographs "The Pyrimidines", ed. by D. J. Brown (1962) and "Pyridine and its Derivatives", ed. by R. A. Abramovitch (1961), Interscience Publishers, Inc., New York, N.Y., and their supplements. The preparation of certain of these intermediates is described in greater detail below.

2,6-Disubstituted-5-amino-pyrimidine derivatives may be prepared by reacting the appropriately substituted 4,6-dihydroxypyrimidine with a nitrating agent such as fuming nitric acid in acetic acid at a temperature from about 15° C. to about 40° C. for a period of about 1 to about 5 hours. The resulting 5-nitropyrimidines are converted to the 2,4-dichloro-5-nitropyrimidine intermediates using a chlorinating agent such as phosphoryl chloride, alone or in the presence of a base, preferably diethylaniline, at a temperature from about 100 to about 115° C. for a period of about 0.5 to about 2 hours. Procedures for carrying out these transformations are described in J. Chem. Soc., 3832 (1954).

The 2,6-bis(alkylthio)-5-nitropyrimidine derivatives may be prepared by reacting the appropriate dichloro intermediate with two equivalents of sodium alkylthiolate in a solvent such as dimethylformamide or, preferably, methanol, for about 4 to about 16 hours at a temperature from about 0 to about 30° C., preferably at ambient temperature. Monosubstitution of the dichloro intermediate is accomplished by using one equivalent of nucleophile, at a reaction temperature of about 0 to about 100° C., depending on the reactivity of the nucleophile, in an inert solvent such as dimethylformamide or tetrahydrofuran, for a period of about 4 to about 16 hours.

The resulting monochloro derivative is then reacted with one equivalent of a different nucleophile to yield a disubstituted derivative with different substituents on the carbon atoms at positions 2 and 4. The 2,6-disubstituted-5-nitropyrimidine is reduced using a reducing agent such as stannous chloride in concentrated hydrochloric acid or hydrogen gas with an appropriate catalyst, to yield the corresponding 5-aminopyrimidine derivative.

The novel pyridines of formula XXVIII and other 2,4-disubstituted-3-aminopyridine derivatives may be prepared by reacting the appropriate 2,4-dihydroxypyridine with a nitrating agent such as concentrated nitric acid at 80–100° C. for 15–60 minutes. For example, the preparation of 2,4-dihydroxy-6-methyl-3-nitropyridine is described in *J. Heterocyclic Chem.*, 1970, 7, 389. The resulting 2,4-dihydroxy-3-nitro-pyridine is sequentially converted to the 2,4-dichloro-3-nitropyridine, 2,4-disubstituted-3-nitro-pyridine and 2,4-disubstituted-3-aminopyridine derivatives, using reaction conditions similar to those described above for the pyrimidine series.

The preparation of certain 5-aminoquinolines and 5-aminoisoquinolines is illustrated in scheme 1. Referring to scheme 1, 5-aminoquinolines and isoquinolines of the formulae XV and XVII may be prepared as follows. A quinoline or isoquinoline of the formula XIII is nitrated at the 5 position, respectively, by reacting it with a nitrating agent such as nitric acid or potassium nitrate with or without an acid catalyst such as sulfuric acid, for from about 2 to 16 hours at a temperature from about 0–100° C. The nitro compound of formula XIV so formed is then reduced using a reducing agent such as stannous chloride, iron, zinc, or hydrogen gas with an appropriate catalyst, with or without an acid catalyst such as hydrochloric acid, for from about 2 to 16 hours at a temperature from about 0–100° C., to yield the corresponding 5-aminoquinoline or 5-aminoisoquinoline of formula XV.

Compounds of the formula XVII, wherein $R^{15}$ is —$SR^{14}$ and is attached to the quinoline or isoquinoline ring at the 6 position, and wherein $R^{14}$ is ($C_1$-$C_6$)alkyl, ($C_5$-$C_7$) cycloalkyl, phenyl ($C_1$-$C_4$) alkyl, phenyl, substituted phenyl, heteroaryl, or substituted heteroaryl, may be prepared as follows. A compound of the formula XIV, wherein $R^5$ is —Cl and is attached to the quinoline or the isoquinoline ring at the 6 position, is reacted with a compound of the formula $R^{14}SH$, wherein $R^{14}$ is as defined above, and a base such as sodium hydride, or such compound of the formula XIV is reacted with a compound of the formula $R^{14}SNa$, wherein $R^{14}$ is as defined above, in an inert solvent such as tetrahydrofuran, for about 4 to 16 hours at a temperature of from about −10° C. to room temperature. The preferred temperature is −10° C. This reaction yields a compound of the formula XVI, which is then converted to the corresponding 5-aminoquinoline or isoquinoline of the formula XVII by the method described above for reduction of compounds of formula XIV.

Treatment of the compound of formula $R^{17}R^{18}NH$ with a compound of the formula $R^1N$=C=Q yields the corresponding urea (Q=O) or thiourea (Q=S) of the formula I. Procedures for the preparation of compounds of the formula $R^1N$=C=Q are known in the literature and several methods are reviewed in "Organic Functional Group Preparations, Vol 1", Chapter 12, Academic Press, New York (1968). The preparation of ureas and thioureas by the reaction of amines with isocyanates and isothiocyanates, respectively, are reviewed in *Organic Functional Group Preparations,* Vol. 2, Chapter 6, Academic Press, New York (1971).

Compounds of the formula $R^1N$=C=O may be obtained by reacting compound of the formula $R^1NH_2$ with 1 to 6 equivalents of an appropriate reagent such as phosgene, trichloromethyl chloroformate or bis(trichloromethyl) carbonate. The reaction is generally carried out in an inert ether, aromatic hydrocarbon or chlorinated hydrocarbon solvent such as dioxane, diisopropyl ether, benzene, toluene, dichloromethane or chloroform. It may be conducted in the presence of a base such as a tertiary amine (e.g., pyridine, triethylamine or quinoline). Reaction temperatures may range from about 0° C. to about 120° C., and are preferably from about 20° C. to about 100° C. Preferably, the heterocyclic amine of formula $R^1NH_2$ is reacted with 1 to 2 equivalents of trichloromethyl chloroformate in refluxing dichloromethane for about 18 hours.

The reaction of compounds of the formula $R^1N$=C=Q with compounds of formula $R^{17}R^{18}NH$ to form compounds of the formula I is carried out in an inert, anhydrous solvent such as chloroform, benzene, dimethylformamide, dioxane or tetrahydrofuran, at a temperature from about 20° C. to 100° C., for about 3 to 30 hours, preferably in dimethylformamide at about 80° C. for about 16 hours.

Amines of the formula $NHR^{17}R^{18}$ may be prepared by a variety of methods well known in the art (see e.g., *Vogel's Textbook of Practical Organic Chemistry,* Longman, Inc., New York, pp. 769–782 and pp. 717–718 (5th ed. 1989), *Organic Functional Group Preparations,* Vol 2. Academic Press, New York, pp. 401–405 (2nd ed. 1983). Other examples of methods for the preparation of amines of the formula $NHR^{17}R^{18}$ are described in EP 0399 422 A1, EP 0415 123 A2 and EP 0439 059 A2.

For instance, compounds of the formula $R^{17}R^{18}NH$ wherein $R^{19}$ is hydrogen and $R^{20}$ is optionally substituted aryl-($C_1$-$C_6$)alkyl or optionally halogenated ($C_1$-$C_{12}$) alkyl may be prepared by treating a compound of the formula Ar—$CH_2$—CN with an alkali metal amide followed by addition of a compound of the formula $R^{20}I$ to form a compound of the formula

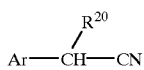

which is subsequently reduced to the amine of the formula

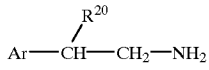

by standard means.

The alkali metal moieties of the amides may be exemplified by lithium, sodium and potassium, preferably lithium. A most preferred amide is lithium diisopropylamide.

The reduction of the nitrites may be effected using borane, e.g. in the form of its complex with tetrahydrofuran, or by hydrogenation in the presence of Raney nickel.

Except where otherwise noted, pressure is not critical in any of the above reactions. Preferred temperatures for the above reactions were stated where known. In general, the preferred temperature for each reaction is the lowest temperature at which product will be formed. The preferred temperature for a particular reaction may be determined by monitoring the reaction using thin layer chromatography.

Preparation of certain novel intermediates useful in preparing the compounds of the invention is described in preparative examples A through R.

The novel compounds of formula I and the pharmaceutically acceptable salts thereof are useful as inhibitors of acyl coenzyme A: cholesterol acyltransferase (ACAT). As such they inhibit intestinal absorption of cholesterol in mammals and are useful in the treatment of high serum cholesterol in mammals, including humans. As used herein, treatment is meant to include both the prevention and alleviation of high serum cholesterol. The compound may be administered to a subject in need of treatment by a variety of conventional routes of administration, including orally, parenterally and topically. In general, these compounds will be administered orally or parenterally at dosages between about 0.08 and about 30 mg/kg body weight of the subject to be treated per day, preferably from about 0.08 to 5 mg/kg. For an adult human of approximately 70 kg of body weight, the usual dosage would, therefore, be about 5.6 to about 2100 mg per day. However, some variation in dosage will necessarily occur depending on the condition of the subject being treated and the activity of the compound being employed. The person responsible for administration will, in any event, determine the appropriate dose for the individual subject.

A compound of formula I or a pharmaceutically acceptable salt thereof may be administered alone or in combination with pharmaceutically acceptable carriers, in either single or multiple doses. Suitable pharmaceutical carriers include inert solid diluents or fillers, sterile aqueous solutions and various organic solvents. The resulting pharmaceutical compositions are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of a compound of formula I or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. Such solutions are especially suitable for intravenous, intramuscular, subcutaneous and intraperitoneal administration. In this connection, the sterile aqueous media employed are all readily available by standard techniques known to those skilled in the art.

The activity of the compounds of the present invention as ACAT inhibitors may be determined by a number of standard biological or pharmacological tests. For example, the following procedure was used to determine the ACAT inhibiting activity of compounds of formula I. ACAT was assayed in microsomes isolated from chow fed Sprague-Dawley rats according to Bilheimer, J. T., *Meth. Enzymol.*, 111, ps 286–293 (1985), with minor modifications. Microsomes from rat liver were prepared by differential centrifugation and washed with assay buffer prior to use. The assay mixture contained 25 μl of BSA (40 mg/ml), 30 μl of rat liver microsome solution (100 μg microsomal protein), 20 μl of assay buffer (0.1 M $K_2PO_4$, 1.0 mM reduced Glutathione, pH 7.4), 20 μg of cholesterol in 100 μl of a 0.6% Triton WR-1339 solution in assay buffer, and 5 μl of test compound dissolved in 100% DMSO (total volume=180 μl). The assay mixture was incubated for 30 min at 37° C. The reaction was started by the addition of 20 μl of $^{14}$C-Oleoyl-CoA solution (1000μM, 2,000 dpm/nmol) and run for 15 min at 37° C. The reaction was stopped by the addition of 1 ml EtOH. The lipids were extracted into 4 ml hexane. A 3 ml aliquot was dried under $N_2$, and resuspended in 100 μl of chloroform. 50 μl of chloroform were spotted on a heat activated TLC plate and developed in hexane: diethyl ether: acetic acid (85:15:1, v:v:v). Incorporation of radioactivity into cholesteryl esters was quantified on a Berthold LB2842 Linear TLC Analyzer. ACAT inhibition was calculated relative to a DMSO control assay.

The activity of the compounds of formula I in inhibiting intestinal absorption of cholesterol may be determined by the procedure of Melchoir and Harwell, *J. Lipid. Res.* 26, 306–315 (1985).

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra ($^{13}$C NMR) were measured for solutions in deuterochoroform (CDCl$_3$) and peak positions are expressed in parts per million (ppm) downfield from tetramethylsilane (TMS). The peak shapes are denoted as follows: s, singlet; d, doublet; t, triplet; q, quartet; q, quintet; hx, hextet; h, heptet; m, multiplet; br, broad; vb, very broad; c, complex.

PREPARATION OF INTERMEDIATES

Preparative Example A

5-Iodo-1,1-difluoropentane

A solution of 5-bromo-1,1-difluoropentane (2.65 g, 14.2 mmol) and sodium iodide (10.63 g, 70.8 mmol) in acetone (150 ml) was refluxed under nitrogen overnight. The reaction mixture was then filtered and the filtrate was concentrated at atmospheric pressure. The residue was dissolved in dichloromethane (50 ml) and the solution was washed with water (2×30 ml) and brine (30 ml), dried (sodium sulfate) and concentrated under reduced pressure at room temperature. The crude product was distilled under reduced pressure to yield the title compound as a yellowish liquid (2.24 g, 93% yield), bp 73–75° C., 10 mm Hg. $^1$H NMR (300 MHz, CDCl$_3$) δ1.59 (m, 2H), 1.84 (c, 4H), 3.2 (t, 2H), 5.63, 5.82, 6.01 (3t, total 1H).

Preparative Example B 2-(2-Chlorobenzo [b]thiophen-3-yl)-7,7-difluoroheptanenitrile A solution of lithium diisopropylamide in cyclohexane (5.13 mmol, 3.42 ml of a 1.5M solution) was added dropwise to a solution of (2-chlorobenzo[b]thiophen-3-yl) acetonitrile (1.06 g, 5.13 mmol) in tetrahydrofuran (10 ml) cooled to −70° C. under nitrogen. The resulting solution was stirred at −70° C. for 20 min, then a solution of 5-iodo-1,1-difluoropentane (1.2 g, 5.13 mmol) in tetrahydrofuran (5 ml) was slowly added at −70° C. The reaction mixture was stirred at −70° C. for 1 hr, then slowly allowed to warm to room temperature and left at that temperature overnight. Water (60 ml) was added to the reaction solution and the resulting mixture was extracted with ethyl acetate (3×70 ml). The combined ethyl acetate extracts were washed with brine (80 ml), dried (sodium sulfate) and concentrated in vacuo. The crude product (2.1 g) was purified by column chromatography on silica gel (200 g), eluting with 4:1 hexane/dichloromethane followed by 7:3 hexane/dichloromethane to yield the title compound as an oil (950 mg, 59% yield). $^1$H NMR (300 MHz, CDCl$_3$) δ1.4–1.7 (c, 4H), 1.7–2.05 (c, 3H), 2.2 (c, 1H) 4.3 (t, 1H), 5.6, 5.78, 5.98 (3t, total 1H), 7.42 (m, 2H), 7.75 (d, 1H), 7.95 (d, 1H).

In a similar manner, the following nitriles were synthesized:

Preparative Example C 2-(naphth-1-yl)-7,7-difluoroheptanenitrile

75% yield $^1$H NMR (300 MHz, CDCl$_3$) δ1.44–1.72 (c, 4H), 1.72–1.94 (c, 2H), 2.07 (m, 2H), 4.57 (t, 1H), 5.6, 5.8, 5.99 (3t, total 1H), 7.44–7.64 (m, 3H), 7.69 (d, 1H), 7.9 (m, 3H).

Preparative Example D 2-(2,5-Dimethylphenyl)-6-phenylhexanenitrile

86% yield $^1$H NMR (300 MHz, CDCl$_3$) δ1.48–2.0 (c, 6H), 2.28 (s, 3H), 2.34 (s, 3H), 2.63 (t, 2H), 3.89 (q, 1H), 7.06 (m, 2H), 7.12–7.32 (m, 6H)

Preparative Example E 2-(2-Chlorobenzo [b]thiophen-3-yl-7,7-difluoroheptanamine A solution of borane-tetrahydrofuran complex in tetrahydrofuran (6.07 mmol, 6.07 ml of a 1.0M solution) was added dropwise to a solution of (2-chlorobenzo[b]thiophen-3-yl)-7,7-difluoroheptanenitrile (950 mg, 3.03 mmol) in tetrahydrofuran (15 ml) at room temperature under nitrogen and the reaction was left at room temperature overnight. Aqueous hydrochloric acid (5 ml of a 3N solution) was then added and reaction mixture was refluxed for 30 min followed by removal of the tetrahydrofuran in vacuo. The resulting aqueous phase was diluted with water (10 ml) and extracted with ethyl acetate (3×30 ml). The combined ethyl acetate extracts were washed with brine (40 ml), dried (sodium sulfate) and concentrated in vacuo. The residue (930 mg) was purified by column chromatography on silica gel (100 g) eluting with 9:1 ethyl acetate/methanol to yield the title compound as an oil (632 mg, 66% yield).

In a similar manner, the following amines were synthesized:

Preparative Example F

[2-(2-Chlorobenzo[b]thiophen-3-yl)-5-methylhexanamine

67% yield $^1$H NMR (300 MHz, CDCl$_3$) δ0.79, 0.80, 0.81, 0.83 (2d, 6H), 0.92–1.08 (m, 1H), 1.1–1.28 (m, 1H), 1.5 (h, 1H), 1.66 (b, 2H), 1.78 (m, 1H), 1.94 (c, 1H), 3.09 (m, 1H), 3.18–3.37 (c, 2H), 7.32 (c, 2H), 7.71 (c, 1H), 7.79 (c, 1H).

Preparative Example G

5-Methyl-2-(5-methylbenzo [b]thiophen-3-yl) hexanamine

53% yield $^1$H NMR (300 MHz, CDCl$_3$) δ0.84 (d, 6H), 1.18 (c, 2H), 1.52 (h, 1H), 1.75 (bq, 2H), 2.02 (b, 2H), 2.49 (s, 3H), 3.0 (d, 2H), 3.12 (p, 1H), 7.1 (s, 1H), 7.17 (d, 1H), 7.59 (s, 1H), 7.73 (d, 1H).

Preparative Example H 2-(Benzo[b]thiophen-3-yl)heptanamine

65% yield $^1$H NMR (300 MHz, CDCl$_3$) δ0.83 (t, 3H), 1.25 (c, 6H), 1.76 (c, 2H), 2.05 (b, 2H), 3.03 (c, 2H), 3.19 (p, 1H), 7.14 (s, 1H), 7.36 (c, 2H), 7.81 (m, 1H), 7.87 (m, 1H).

Preparative Example I 2-(Benzo[b]thiophen-3-yl)-6-methylheptanamine

66% yield $^1$H NMR (300 MHz, CDCl$_3$) δ0.78, 0.80, 0.81, 0.82 (2d, 6H), 1.1–1.44 (c, 4H), 1.47 (h, 1H), 1.74 (q, 2H), 2.06 (b, 2H), 3.04 (c, 2H), 3.19 (p, 1H), 7.14 (s, 1H), 7.36 (c, 2H), 7.84 (m, 2H).

Preparative Example J 2-(5-Methylbenzo [b]thiophen-3-yl)-6,6,6trifluorohexanamine 51% yield $^1$H NMR (300 MHz, CDCl$_3$) δ1.54 (m, 2H), 1.69 (b, 2H), 1.86 (c, 2H), 2.06 (m, 2H), 2.49 (s, 3H), 3.03 (d, 2H), 3.16 (p, 1H), 7.12 (s,1H), 7.19 (d, 1H), 7.57 (s, 1H), 7.75 (d, 1H).

Preparative Example K 2-(2-Chlorobenzo[b]thiophen-3-yl)-6,6,6-trifluorohexanamine 60% yield $^1$H NMR (300 MHz, CDCl$_3$) δ1.35–1.7 (c, 4H), 1.89 (c, 1H), 2.05 (c, 3H), 3.09 (q, 1H), 3.2–3.4 (c, m, 2H), 7.34 (m, 2H), 7.75 (m, 2H).

Preparative Example L 2-(2-Chlorobenzo [b]thiophen-3-yl)heptanamine

68% yield $^1$H NMR (300 MHz, CDCl$_3$) δ0.81 (t, 3H), 1.2 (c, 6H), 1.65 (b, 2H), 1.78 (c, 1H), 1.95 (c, 1H), 3.07 (q, 1H), 3.16–3.38 (c, m, 2H), 7.32 (c, 2H), 7.72 (m, 1H), 7.8 (m, 1H).

Preparative Example M 2-(5-Chlorobenzo[b]thiophen-3-yl)heptanamine

60% yield $^1$H NMR (300 Mhz, CDCl$_3$) δ0.84 (t, 3H), 1.26 (c, 6H), 1.65–1.9 (c, 4H), 3.0 (d, 2H), 3.1 (p, 1H), 7.19 (s, 1H), 7.29, 7.30, 7.32, 7.33 (q, 1H), 7.77 (m, 2H).

Preparative Example N

2-(5-Methylbenzo[b]thiophen-3-yl)heptanamine

63% yield $^1$H NMR (300 MHz, CDCl$_3$) δ0.84 (t, 3H), 1.26 (c, 6H), 1.76 (c, 2H), 1.84 (b, 2H), 2.49 (s, 3H), 3.0 (d, 2H), 3.13 (p, 1H), 7.1 (s, 1H), 7.18 (d, 1H), 7.6 (s, 1H), 7.74 (d, 1H).

Preparative Example O

2-(5-Chlorobenzo[b]thiophen-3-yl)-6,6,6-trifluorohexanamine

33% yield $^1$H NMR (300 MHz, CDCl$_3$) δ1.43–2.0 (c, 6H), 2.08 (m, 2H), 3.02 (c, 2H), 3.12 (m, 1H), 7.22 (s, 1H), 7.31, 7.32, 7.34, 7.35 (q, 1H), 7.75, 7.76, 7.77, 7.8 (q, 2H).

Preparative Example P

2-(5-Chlorobenzo[b]thiophen-3-yl)-6-methylheptanamine

69% yield $^1$H NMR (300 MHz, CDCl$_3$) δ0.79, 0.81, 0.82, 0.83 (2d, 6H), 1.1–1.33 (c, 4H), 1.47 (h, 1H), 1.62–1.93 (c, 4H), 3.01 (d, 2H), 3.11 (p, 1H), 7.2 (s, 1H) 7.29, 7.30, 7.32, 7.33 (q, 1H), 7.76, 7.77, 7.78, 7.784 (q, 2H).

Preparative Example Q

2-(Naphth-1-yl)-7,7-difluoroheptanamine

A mixture of 2-(naphth-1-yl)-7,7-difluoroheptanenitrile (413 mg, 1.51 mmol), Raney nickel (413 mg) and ammonia (0.9 g) in methanol (20 ml) was hydrogenated under 340 kPa (50 psi) hydrogen overnight at room temperature. The mixture was filtered and the filtrate was concentrated in vacuo. The residue was partitioned between ethyl acetate (50 ml) and water (40 ml) and the ethyl acetate extract was washed with brine (30 ml), dried (sodium sulfate) and concentrated in vacuo. The residue (400 mg) was purified by column chromatography on silica gel (100 g), eluting with 85:15 ethyl acetate/methanol to yield the title compound as an oil (321 mg, 77% yield). $^1$H NMR (300 MHz, CDCl$_3$) δ1.35 (c, 6H), 1.78 (c, 4H), 3.08 (c, 2H), 3.61 (c, 1H), 5.52, 5.71, 5.9 (3t, total 1H), 7.37 (d, 1H), 7.5 (m, 3H), 7.75 (d, 1H), 7.88 (d, 1H), 8.16 (d, 1H).

The following compound was synthesized in a similar manner:

Preparative Example R

2-(2,5-Dimethylphenyl)-6-phenylhexanamine

74% yield $^1$H NMR (300 MHz, CDCl$_3$) δ1.15–1.44 (c, 4H), 1.5–1.75 (c, 4H), 2.29 (s, 3H), 2.32 (s, 3H), 2.55 (m, 2H), 2.9 (c, 3H), 6.91, 6.94, 6.95 (t, 2H), 7.05 (d, 1H), 7.14 (m, 3H), 7.29 (t, 2H).

EXAMPLE 1

N-[2,4-Bis(methylthio)-6-methylpyridin-3-yl]-N'-(indan-2-yl)-N'-(4-isopropylbenzyl)urea A solution of 2-(4-isopropylbenzylamino)indane (159 mg, 0.6 mmol) and 2,4-bis(methylthio)-6-methylpyridin-3-yl isocyanate (136 mg, 0.6 mmol) in 3 ml dimethylformamide was heated at 80° C. under nitrogen overnight. The reaction mixture was cooled to room temperature, diluted with 50 ml ethyl acetate and washed with 3×50 ml water, then 50 ml brine, dried (sodium sulfate), filtered and concentrated in vacuo. The solid residue (265 mg) was purified by column chromatography on silica gel (150 g), eluting with 7:3 hexane/ethyl acetate to yield the title compound as a white solid (195 mg, 66% yield).

$^1$H NMR (300 MHz, CDCl$_3$ δ1.25 (d, 6H), 2.36 (s, 3H), 2.45 (s, 3H), 2.47 (s, 3H), 2.91 (h, 1H), 3.06 (dd, 2H), 3.31 (dd, 2H), 4.57 (s, 2H), 5.39 (p, 1H), 5.57 (s, 1H), 6.59 (s, 1H), 7.15 (c, 4H), 7.22–7.35 (m, 4H).

The 1- and indan-2-yl urea derivatives of Examples 2–18 were synthesized in a similar manner.

EXAMPLE 2

N-[2,4-Bis(methylthio)-6-methylpyridin-3-yl]-N'-(2,5-dimethylbenzyl)-N'-(indan-2-yl)urea 66% yield.

$^1$H NMR (300 MHz, CDCl$_3$) δ2.15 (s, 3H), 2.37 (s, 3H), 2.39 (s, 3H), 2.45 (s, 3H), 2.47 (s, 3H), 2.99 (dd, 2H), 3.29 (dd, 2H), 4.47 (s, 2H), 5.48 (s) and 5.50 (m) (total 2H), 6.58 (s, 1H), 7.04 (m, 2H), 7.15 (c, 5H), 7.43 (s, 1H).

EXAMPLE 3

N-[2,4-Bis(methylthio)-6-methylpyridin-3-yl]-N'-(2,4-dimethylbenzyl)-N'-(indan-2-yl)urea 66% yield.

$^1$H NMR (300 MHz, CDCl$_3$) δ2.17 (s, 3H), 2.33 (s, 3H), 2.37 (s, 3H), 2.45 (s, 3H), 2.48 (s, 3H), 2.99 (dd, 2H), 3.26 (dd, 2H), 4.48 (s, 2H), 5.44 (m) and 5.49 (s) (total 2H), 6.58 (s, 1H), 6.99 (s, 1H), 7.14 (c, 5H), 7.47 (d, 1H).

EXAMPLE 4

N-[4,6-Bis(methylthio)-2-methylpyrimidin-5-yl]-N'-(indan-2-yl)-N'-(4-isopropylbenzyl)urea 62% yield.

$^1$H NMR (300 MHz, CDCl$_3$) δ1.25 (d, 6H), 2.46 (s, 6H), 2.56 (s, 3H), 2.92 (h, 1H), 3.04 (dd, 2H), 3.31 (dd, 2H), 4.55 (s, 2H), 5.41 (m) and 5.46 (s) (total 2H), 7.16 (c, 4H), 7.23–7.34 (m, 4H).

EXAMPLE 5

N-[4,6-Bis(methylthio)-2-methylpyrimidin-5-yl]-N'-(2,4-dimethylbenzyl)-N'-(indan-2-yl)urea 70% yield.

$^1$H NMR (300 MHz, CDCl$_3$) δ2.17 (s, 3H), 2.33 (s, 3H), 2.47 (s, 6H), 2.56 (s, 3H), 2.99 (dd, 2H), 3.28 (dd, 2H), 4.46 (s, 2H), 5.41 (s) and 5.44 (m) (total 2H), 6.9 (m, 1H), 7.14 (c, 5H), 7.44 (d, 1H).

EXAMPLE 6

N-(2,5-Dimethylbenzyl)-N-(indan-2-yl-N'-(6-methylthioquinolin-5-yl)urea

19% yield. $^1$H NMR (300 MHz, CDCl$_3$) δ2.20 (s, 3H), 2.45 (s, 6H), 3.06 (dd, 2H), 3.34 (dd, 2H), 4.60 (s, 2H), 5.54 (p, 1H), 6.20 (s, 1H), 7.07 (m, 2H), 7.16 (c, 4H), 7.38 (1, 1H), 7.46 (s, 1H), 7.60 (d, 1H), 7.96 (d, 1H), 8.07 (d, 1H), 8.82 (m, 1H).

EXAMPLE 7

N-[2,4-Bis-methylthio)-6-methylpyridin-3-yl]-N'-(2-chlorobenzyl)-N'-(indan-2-yl)urea 17% yield.

$^1$H NMR (300 MHz, CDCl$_3$) δ2.38 (s, 3H), 2.45 (s, 3H), 2.48 (s, 3H), 3.02 (dd, 2H), 3.26 (dd, 2H), 4.67 (s, 2H), 5.37 (p, 1H), 5.51 (s, 1H), 6.59 (s, 1H). 7.14 (q, 4H), 7.25 (c, 1H), 7.38 (c, 2H), 7.64 (d, 1H).

EXAMPLE 8

N-[4,6-Bis(methylthio)-2-methylpyrimidin-5-yl]-N'-(2,5-dimethylbenzyl-N'-(indan-2-yl)urea 69% yield.

$^1$H NMR (300 MHz, CDCl$_3$) δ2.15 (s, 3H), 2.39 (s, 3H), 2.47 (s, 6H), 2.57 (s, 3H), 2.98 (dd, 2H), 3.29 (dd, 2H), 4.45 (s, 2H), 5.40 (s, 1H), 5.50 (p, 1H), 7.06 (m, 2H), 7.14 (m, 4H), 7.38 (s, 1H).

EXAMPLE 9

N-[4,6-Bis(methylthio)-2-methylpyrimidin-5-yl]-N'-(indan-2-yl)-N'-[4-(3-methylbutyl)benzyl]urea 71% yield.

$^1$H NMR (300 MHz, CDCl$_3$) δ0.93 (d, 6H), 1.45–1.69 (c, 3H), 2.47 (s, 6H), 2.57 (s) and 2.61 (m) (total 5H), 3.03 (dd, 2H), 3.31 (dd, 2H), 4.55 (s, 2H), 5.40 (m) and 5.46 (m) (total 2H), 7.10–7.33 (c, 8H).

EXAMPLE 10

N-[2,4-Bis(methylthio)-6-methylpyridin-3-yl]-N'-(indan-2-yl)-N'-[4-(3-methylbutyl)benzyl]urea 58% yield.

$^1$H NMR (300 MHz, CDCl$_3$) δ0.92 (d, 6H), 1.44–1.68 (c, 3H), 2.36 (s, 3H), 2.44 (s, 3H), 2.46 (s, 3H), 2.60 (m, 2H), 3.04 (dd, 2H), 3.30 (dd, 2H), 4.56 (s, 2H), 5.39 (p, 1H), 5.54 (s, 1H), 6.58 (s, 1H), 7.10–7.34 (c, 8H).

EXAMPLE 11

N-[2,4-Bis(methylthio)-6-methylpyridin-3-yl]-N'-(indan-1-yl)-N'-(naphth-1-ylmethyl)urea 25% yield.

$^1$H NMR (300 MHz, CDCl$_3$) δ2.1 (c, 1H), 2.32–2.54 [total 10H, including 2.4 (s, 3H), 2.46 (s, 3H), 2.51 (s, 3H)], 2.83 (c, 2H), 4.69 (d, 1H), 5.26 (d, 1H), 5.5 (b, 1H), 6.06 (vb, 1H), 6.6 (s, 1H), 7.15–7.39 (c, 4H), 7.5 (c, 3H), 7.72–8.0 (c, 4H).

EXAMPLE 12

N[2,4-Bis(methylthio)-6-methylpyridin-3-yl]-N'-(indan-1-yl)-N'-(naphth-2-10 ylmethyl)urea 32% yield.

$^1$H NMR (300 MHz, CDCl$_3$) δ2.1 (c, 1H), 2.33–2.55 [total 10H, including 2.37 (s, 3H), 2.47 (s, 3H), 2.49 (s, 3H)], 2.88 (c, 2H), 4.5 (d, 1H), 4.8 (d, 1H), 5.6 (b, 1H), 6.08 (vb, 1H), 6.6 (s, 1H), 7.22 (c, 3H), 7.47–7.54 (c, 4H), 7.83 (c, 3H), 7.93 (s, 1H).

EXAMPLE 13

N-[2,4-Bis(methylthio)-6methylpyridin-3-yl]-N'-(indan-1 -yl)-N'-(4-t-butylbenzyl)urea 23% yield.

$^1$H NMR (300 MHz, CDCl$_3$) δ1.32 (s, 9H), 2.1 (c, 1H), 2.36–2.55 [total 10H, including 2.38 (s, 3H), 2.46 (s, 3H), 2.48 (s, 3H)], 2.9 (c, 2H), 4.29 (d, 1H), 4.6 (d, 1H), 5.52 (b, 1H), 6.05 (vb, 1H), 6.6 (s, 1H), 7.22 (c, 4H), 7.32 (d, 2H), 7.39 (d, 2H).

EXAMPLE 14

N-[2,4-Bis(methylthio)-6-methylpyridin-3-yl]-N'-[indan-1-yl)-N'-(4-phenylbenzyl)urea 28% yield.

$^1$H NMR (300 MHz, CDCl$_3$) δ2.1 (c, 1H), 2.38–2.58 [total 10H, including 2.39 (s, 3H), 2.47 (s, 3H), 2.5 (s, 3H)], 2.9 (c, 2H), 4.4 (d, 1H), 4.7 (d, 1H), 5.54 (b, 1H), 6.02 (vb, 1H), 6.61 (s, 1H), 7.24 (c, 4H), 7.31–7.52 (c, 51H), 7.6 (c, 4H).

EXAMPLE 15

N-[2,4-Bis(methylthio)-6-methylpyridin-3-yl]-N'-(indan-2-yl)-N'-(naphth-1-ylmethyl)urea 20% yield.

$^1$H NMR (300 MHz, CDCl$_3$) δ2.4 (s, 3H), 2.48 (s, 3H), 2.53 (s, 3H), 3.07 (dd, 2H), 3.33 (dd, 2H), 5.1 (s, 2H), 5.5 (m) and 5.57 (s) (total 2H), 6.6 (s, 11H), 7.12 (c, 4H), 7.48–7.64 (c, 3H), 7.76–7.97 (c, 4H).

EXAMPLE 16

N-[2,4-Bis(methylthio)-6-methylpyridin-3-yl]-N'-(indan-2-yl)-N'-(naphth-2-ylmethyl)urea 20% yield.

$^1$H NMR (300 MHz, CDCl$_3$) δ2.37 (s, 3H), 2.48 (s, 6H), 3.1 (dd, 2H), 3.34 (dd, 2H)$_1$ 4.78 (s, 2H), 5.47 (p, 1H), 5.68 (s, 1H), 6.6 (s, 1H), 7.15 (c, 4H), 7.38–7.58 (c, 3H), 7.87 (c, 3H), 7.95 (s, 1H).

EXAMPLE 17

N-[2,4-Bis(methylthio)-6-methylpyridin-3-yl]-N'-(indan-2-yl)-N'-(naphth-2-ylmethyl)-N'-(2,4,6-trimethylbenzyl)urea 13% yield.

$^1$H NMR (300 MHz, CDCl$_3$) δ2.27 (s, 3H), 2.38 (s, 3H), 2.4 (s, 6H), 2.46 (s, 3H), 2.5 (s, 3H), 3.07 (dd, 2H), 3.55 (dd, 2H), 4.16 (m, 1H), 4.77 (s, 2H), 5.41 (s, 1H), 6.6 (s, 1H), 6.88 (s, 2H), 7.12 (c, 4H).

EXAMPLE 18

N-[2,4-Bis(methylthio)-6-methylpyridin-3-yl]-N'-(2,3-dichlorobenzyl)-N'-(indan-2-yl)urea 27% yield.

$^1$H NMR (300 MHz, CDCl$_3$) δ2.41 (s, 3H), 2.49 (s, 3H), 2.52 (s, 3H), 3.0 (dd, 2H), 3.28 (dd, 2H), 4.68 (s, 2H), 5.32 (q, 1H), 5.54 (s, 1H), 6.63 (s, 1H), 7.16 (c, 4H), 7.34 (t, 1H), 7.45 (d, 1H), 7.55 (d, 1H).

EXAMPLE 19

N-[2,4-Bis(ethylthio)-6methythpyridin-3-yl]-N'-cycloheptyl-N'-(4-phenylbenzyl)urea 33% yield.

$^1$H NMR (300 MHz, CDCl$_3$) δ1.28, 1.32 (2t, 6H), 1.4–1.8 (C, 10H), 2.02 (c, 2H), 2.42 (s, 3H), 2.86 (q, 2H), 3.09 (q,

2H), 4.37 (c, 1H), 4.62 (s, 2H), 5.54 (s, 1H), 6.62 (s, 1H), 7.34 (t, 1H), 7.44 (t, 2H), 7.51 (d, 2H), 7.6 (m, 4H).

EXAMPLE 20

N-[2,4-Bis(ethylthio)-6methythpyridin-3-yl]-N'-cycloheptyl-N'-(fluoren-2-ylmethyl)urea 40% yield.

$^1$H NMR (300 MHz, CDCl$_3$) δ1.22, 1.24, 1.26, 1.27, 1.3 (2t, 6H), 1.4–1.8 (c, 10H), 2.02 (c, 2H), 2.41 (s, 3H), 2.84 (q, 2H), 3.06 (q, 2H), 3.91 (s, 2H), 4.42 (c, 1H), 4.65 (s, 2H), 5.55 (s, 1H), 6.6 (s,1H), 7.25–7.44 (m, 3H), 7.54 (d, 1H), 7.68 (s, 1H), 7.78 (d, 2H),

EXAMPLE 21

N-[2,4-Bis(ethylthio)-6-methylpyridin-3-yl]-N'-cycloheptyl-N'-(naphth-2-ethyl)urea 31% yield $^1$H NMR (300 MHz, CDCl$_3$) δ1.2, 1.22, 1.25, 1.27, 1.3 (2t, 6H), 1.4–1.8 (c, 1OH), 2.04 (c, 2H), 2.4 (s, 3H), 2.82 (q, 2H), 3.04 (q, 2H), 4.47 (c, 1H), 4.73 (s, 2H), 5.6 (s, 1H), 6.59 (s, 1H), 7.48 (c, 3H), 7.85 (m, 3H), 7.99 (s, 1H).

EXAMPLE 22

N-[2.4-Bis(ethylthio)-6-methylpyridin-3-yl]-N'-heptyl-N'-[naphth-2-ylmethyl]urea 33% yield.

$^1$H NMR (300 MHz, CDCl$_3$) δ0.86 (t, 3H), 1.2–142 (c, 14H), 1.72 (c, 2H), 2.43 (s, 3H), 2.88 (q, 2H), 3.11 (q, 2H), 3.44 (t, 2H), 4.79 (s, 2H), 5.73 (s, 11H), 6.65 (s, 1H), 7.48 (m, 3H), 7.85 (m, 4H).

EXAMPLE 23

N-[2,4-Bis(ethylthio)-methylpyridin-3-yl]-N'-heptyl-N'-(2,4,6-trimethylbenzyl)urea 34% yield.

$^1$H NMR (300 MHz, CDCl$_3$) δ0.86 (t, 3H), 1.23 (c, 8H), 1.3, 1.32, 1.33, 1.35, 1.36, 1.38 (2t, 6H), 1.65 (c, 2H), 2.27 (s, 3H), 2.36 (s, 6H), 2.46 (s, 3H), 2.91 (q, 2H), 3.05 (t, 2H), 3.15 (q, 2H), 4.71 (s, 2H), 5.7 (s, 1H), 6.68 (s, 1H), 6.87 (s, 2H).

EXAMPLE 24

N-[2,4-Bis(methylthio)-methylpyridin-3-yl]-N'-cycloheptyl-N'-(4-phenylbenzyl)urea 17% yield.

$^1$H NMR (300 MHz, CDCl$_3$) δ1.4–1.77 (c, 101H), 2.02 (c, 2H), 2.36 (s, 3H), 2.45 (s, 3H), 2.46 (s, 3H), 4.38 (c, 1H), 4.62 (s, 2H), 5.51 (s, 1H), 6.58 (s, 1H), 7.34 (t,1H), 7.4–7.54 (m, 4H), 7.61 (t, 4H).

EXAMPLE 25

N-[2,4-Bis(methylthio)-6-methylpyridin-3-yl]-N'-cycloheptyl-N'-(fluoren-2-ylmethyl)urea 9% yield.

$^1$H NMR (300 MHz, CDCl$_3$) δ1.4–1.8 (c, 10H), 2.02 (c, 2H), 2.35 (s, 3H), 2.43 (s, 3H), 2.44 (s, 3H), 3.91 (s, 2H), 4.42 (c, 1H), 4.66 (s,1H), 5.52 (s,1H), 6.57 (s, 1H), 7.24–7.45 (m, 3H), 7.55 (d, 11H), 7.67 (s, 11H), 7.79 (d, 2H).

EXAMPLE 26

N-[2,4-Bis(ethylthio)-6-methylpyridin-3-yl]-N'-(4-isopropylbenzyl)-N'-(1,2,3,4-tetrahydronaphth-2-yl)urea 13% yield.

$^1$H NMR (300 MHz, CDCl$_3$) δ1.25, 1.26, 1.27, 1.29, 1.31, 1.34, 1.36 (2t and d, 12H), 1.88 (m, 1H), 2.13 (c, 1H), 2.42 (s, 3H), 2.8–3.02 (m and q, 6H), 3.02–3.18 (c and q, 3H), 4.61 (s, 2H), 4.78 (c, 1H), 5.62 (s, 1H), 6.63 (s, 1H), 7.08 (s, 4H), 7.26 (d, 2H), 7.4 (d, 2H).

EXAMPLE 27

N-[2,4-Bis(ethylthio)-6-methylpyridin-3-yl]-N'-heptyl-N'-(3-methylbenzo[b]thiophen-2-ylmethyl)urea 35% yield.

$^1$H NMR (300 MHz, CDCl$_3$) δ0.87 (t, 3H), 1.29–1.9 [c including 2t (1.26, 1.28, 1.29, 1.31,1.32), total 14H], 1.75 (c, 2H), 2.42 (s, 3H), 2.45 (s, 3H), 2.88 (q, 2H), 3.11 (q, 2H), 3.36 (t, 2H), 4.86 (s, 2H), 5.77 (s, 1H), 6.67 (s, 1H), 7.28–7.4 (m, 2H), 7.66 (d, 1H), 7.79 (d, 1H).

EXAMPLE 28

N-[2,4-Bis(ethylthio)-6-methylpyridin-3-yl-N'-(1,2,3,4-tetrahydronaphth-2-yl)-N'-(2,4,6-trimethylbenzyl)urea 26% yield $^1$H NMR (300 MHz, CDCl$_3$) δ1.32, 1.36 (2t, 6H), 2.06 (c, 1H), 2.15–2.35 [c and s (2.25), total 4H], 2.42 (s, 6H), 2.44 (s, 3H), 2.6–2.96 (c, 5H), 3.14 (q, 2H), 3.42 (m, 1H), 3.73 (c, 1H), 4.74 (s, 2H), 5.75 (s, 1H), 6.66 (s, 1H), 6.84 (s, 2H), 7.06 (c, 4H).

EXAMPLE 29

N-[2,4-Bis(methylthio-6-methylpyridin-3-yl]-N'-cycloheptyl-N'-(naphth-2-vimethyl)urea 18% yield $^1$H NMR (300 MHz, CDCl$_3$) δ1.49–1.74 (c, 10H), 2.04 (c, 2H), 2.33 (s, 3H), 2.43 (s, 6H), 4.45 (c, 1H), 4.74 (s, 2H), 5.57 (s, 1H), 6.56 (s, 1H), 7.48 (c, 3H), 7.85 (c, 3H), 7.97 (s, 1H).

EXAMPLE 30

N-[2,4-Bis(ethylthio)-6-methylpyridin-3-yl]-N'-(indan-2-yl)-N'-(4-isopropylbenzyl)urea 17% yield $^1$H NMR (300 MHz, CDCl$_3$) δ1.26 (d) and 1.29, 1.34 (2t) (total 12H), 2.42 (s, 3H), 2.82–2.98 (m, 3H), 3.0–3.14 (m, 4H), 3.31 (dd, 2H), 4.57 (s, 2H), 5.41 (p, 1H), 5.58 (s, 1H), 6.63 (s, 1H), 7.15 (c, 4H), 7.25 (d, 2H), 7.33 (d, 2H).

EXAMPLE 31

N-[2,4-Bis(ethylthio-6-methylpyridin-3-yl]-N'-(2.4-dimethylbenzyl)-N'-(indan-2-yl)urea 43% yield $^1$H NMR (300 MHz, CDCl$_3$ δ1.31, 1.35 (2t, 6H), 2.18 (s, 3H), 2.33 (s, 3H), 2.43 (s, 3H), 2.89 (q, 2H), 3.0 (dd, 2H), 3.11 (q, 2H), 3.29 (dd, 2H), 4.49 (s, 2H), 5.44 (p, 1H), 5.52 (s, 1H), 6.63 (s, 1H), 6.99 (s, 1H), 7.1–7.2 (c, 5H), 7.49 (d, 1H).

EXAMPLE 32

N-[2,4-Bis(methylthio)-6methylpyridin-3-yl]-N'-(4-isopropylbenzyl)-N'-(6,7,8,9-tetrahydro-5H-benzocyclohepten-7-yl)urea 39% yield $^1$H NMR (300 MHz, CDCl$_3$) δ1.24 (d, 6H), 1.45–1.6 (m, 2H), 2.22 (c, 2H), 2.36 (s, 3H), 2.46 (s, 3H), 2.7–2.96 (m, 6H), 4.45 (s, 2H), 4.72 (c, 1H), 5.52 (s, 1H), 6.59 (s, 1H), 7.1 (m, 4H), 7.23 (d, 2H), 7.31 (d, 2H).

EXAMPLE 33

N-[2,4-Bis(ethylthio)-6-methylpyridin-3-yl]-N'-(indan-2-yl)-N'-(2,4,6-trimethylbenzyl)urea 27% yield $^1$H NMR (300 MHz, CDCl$_3$ δ1.3, 1.34 (2t, 6H), 2.27 (s, 3H), 2.4 (s, 6H), 2.41 (s, 3H), 2.88 (q, 2H), 2.98–3.18 (m, 4H), 3.57 (dd, 2H), 4.16 (p, 1H), 4.77 (s, 2H), 5.43 (s, 1H), 6.62 (s, 1H), 6.87 (s, 2H), 7.11 (c, 4H).

EXAMPLE 34

N-[2,4-Bis(methylthio)-6methylpyridin-3-yl]-N'-[2-2-diphenylethyl]urea

A solution of 2,2-diphenylethylamine (148 mg, 0.75 mmol) and 2,4-bis(methylthio)-6-methylpyridin-3yl isocyanate (170 mg, 0.75 mmol) in 15 ml dichloromethane was refluxed under nitrogen overnight. The reaction mixture was then cooled to room temperature and concentrated in vacuo. The residual solid was purified by column chromatography on silica gel (200 g), eluting with 8:2 dichloromethane/ethyl acetate to yield the title compound as white solid (111 mg, 35% yield).

$^1$H NMR (300 MHz, CDCl3) δ2.29 (s, 3H), 2.46 (s, 3H), 2.50 (s, 3H), 3.82 (q, 2H), 4.18 (t, 1H), 6.53 (s, 1H), 7.12–7.28 (c, 12H).

The (2,2-diphenylethyl)urea derivatives of Examples 35–37 were prepared according to the method of Example 34.

EXAMPLE 35

N-(2,2-Diphenylethyl)-N'-(6-methylthioquinolin-5-yl)urea

63% yield.

$^1$H NMR (300 MHz, CDCl$_3$) δ2.27 (s, 3H), 3.62 (bd, 2H), 3.98 (t, 1H), 6.39 (b, 1H), 6.88–7.08 (c, 10H), 7.54 (q, 1H), 7.62 (d, 1H), 7.95 (s, 1H), 8.27 (d, 1H), 8.39 (d, 1H), 8.64 (m, 1H).

EXAMPLE 36

N-[4,6-Bis(methylthio)-2-methylpyrimidin-5-yl]-N'-(2,2-diphenylethyl)urea

80% yield.

$^1$H NMR (CDCl$_3$) δ2.42 (s, 6H), 2.60 (s, 3H), 3.82 (bm, 2H), 4.19 (t, 1H), 4.50 (b, 1H), 5.07 (b, 1H), 7.09–7.27 (c, 10H).

EXAMPLE 37

N-[4,6-Bis(methylthio)pyrimidin-5-yl]-N'-(2,2-diphenylethyl)urea

49% yield.

$^1$H NMR (300 MHz, CDCl$_3$) δ2.43 (s, 3H), 3.84 (q, 2H), 4.20 (t,1H), 4.43 (c, 1H), 5.46 (s, 1H), 7.12–7.31 (c, 10H), 8.59 (s, 1H).

EXAMPLE 38

N-[2,4-Bis(methylthio)-6-methylpyridin-3-yl]-N'-1(-phenylcyclopentyl)methyl]urea A solution of (1-phenylcyclopentyl)methylamine (140 mg, 0.8 mmol) and 2,4-bis(methylthio)-6-methylpyridin-3-yl isocyanate (180 mg, 0.8 mmol) in 3 ml dimethylformamide was heated at 80° C. under nitrogen overnight. The reaction mixture was cooled to room temperature and diluted with 70 ml ethyl acetate. The resulting solution was washed with 3×60 ml water and 60 ml brine, dried (sodium sulfate), filtered and concentrated in vacuo. The residue was chromatographed on silica gel (200 g), eluting with 1:1 ethyl acetate/hexane to yield the title compound as a white solid (90 mg, 28% yield).

$^1$H NMR (300 MHz, CDCl$_3$) δ1.6–1.9 (c, 6H), 2.03 (c, 2H), 2.35 (s, 3H), 2.49 (s, 3H), 2.51 (s, 3H), 3.27 (d, 2H), 4.07 (b, 1H), 5.38 (b, 1H), 6.55 (s, 1H), 7.12 (c, 5H).

The urea derivatives of Examples 39–46 were prepared according to the method of Example 38.

EXAMPLE 39

N-(6-Methylthioquinolin-5-yl)-N'-[(1-phenylcyclopentyl)methyl]urea

31% yield.

$^1$H NMR (300 MHz, CDCl$_3$) δ1.59–1.96 (c, 8H), 2.50 (s, 3H), 3.25 (d, 2H), 3.91 (b, 1H), 5.96 (bs, 1H), 6.81 (c, 2H), 6.95 (c, 3H), 7.41 (q, 1H), 7.57 (d, 1H), 8.05 (d, 1H), 8.22 (d, 1H), 8.86 (m, 1H).

EXAMPLE 40

N-[2,4-Bis(methylthio)-6-methylpyridin-3-yl]-N'-[{1-(4-methylphenyl)cyclopentyl}methyl]urea 24% yield.

$^1$H NMR (300 MHz, CDCl$_3$) δ1.6–1.9 (c, 6H), 2.0 (c, 2H), 2.27 (s, 3H), 2.35 (s, 3H), 2.49 (s, 3H), 2.51 (s, 3H), 3.24 (d, 2H), 4.06 (b,1H), 5.36 (b, $_1$H), 6.51 (s, 1H), 6.98 (q, 4H).

EXAMPLE 41

N-[{1-(4-Methylphenyl)cyclopentyl}methyl-N'-(6-methylthioquinolin-5-yl]urea

28% yield.

$^1$H NMR (300 MHz, CDCl$_3$) δ1.6–1.98 (c, 8H), 2.19 (s, 3H), 2.52 (s, 3H), 3.25 (d, 2H), 3.98 (b, 1H), 5.95 (b, 1H), 6.74 (q, 4H), 7.43 (q, 1H), 7.60 (d, 1H), 8.11 (d, 1H), 8.24 (d, 1H), 8.87 (m, 1H).

EXAMPLE 42

N-(6-Methylthioquinolin-5-yl)-N'-[(1-phenylcyclohexyl)methyl]urea

37% yield.

$^1$H NMR (300 MHz, CDCl$_3$) δ1.18–1.62 (c, 8H), 1.96 (c, 2H), 2.51 (s, 3H), 3.25 (d, 2H), 3.86 (b, 1H), 5.99 (b, 1H), 6.97 (c, 5H), 7.43 (q, $_1$H), 7.58 (d, 1H), 8.09 (d, 1H), 8.23 (d, 1H), 8.85 (m, $_1$H).

EXAMPLE 43

N-[2,4-Bis(methylthio)-6-methylpyridin-3-yl]-N'-[(1-phenylcyclohexyl)methyl]urea 42% yield.

¹H NMR (300 MHz, CDCl₃) δ1.22–1.72 (c, 8H), 2.08 (c, 2H), 2.35 (s, 3H), 2.50 (s, 3H), 2.51 (s, 3H), 3.25 (d, 2H), 3.95 (b, 1H), 5.38 (b, 1H), 6.51 (s, 1H), 7.05–7.25 (c, 5H).

EXAMPLE 44

N-[{1-(4-Methylphenyl)cyclohexyl}methyl]-N'-(6-methylthioquinolin-5-yl)urea

42% yield.

¹H NMR (300 MHz, CDCl₃) δ1.15–1.6 (c, 8H), 1.93 (c, 2H), 2.18 (s, 3H), 2.15 (s, 3H), 3.22 (d, 2H), 3.81 (b, 1H), 5.94 (b, 1H), 6.77 (b, 4H), 7.41 (q, 1H), 7.59 (d, 1H), 8.07 (d, 1H), 8.21 (d, 1H), 8.86 (m, 1H).

EXAMPLE 45

N-[4,6-Bis(methylthio)-2-methylpyrimidin-5-yl]-N'-[{1-(4-methylphenyl)cyclohexyl}methyl]urea 42% yield.

¹H NMR (300 MHz, CDCl₃) δ1.23–1.68 (c, 8H), 2.06 (c, 2H), 2.30 (s, 3H), 2.47 (s, 6H), 2.62 (s, 3H), 3.23 (d, 2H), 3.89 (b, 1H), 5.27 (b, 1H), 7.04 (q, 4H).

EXAMPLE 46

N-[2,4-Bis(methylthio)-6-methylpyridin-3-yl]-N'-[{1-(4-methylphenyl)cyclohexyl}methyl]urea 24% yield.

¹H NMR (300 MHz, CDCl₃) δ1.2–1.7 (c, 8H), 2.06 (c, 2H), 2.28 (s, 3H), 2.35 (s, 3H), 2.50 (s, 3H), 2.52 (s, 3H), 3.22 (d, 2H), 3.95 (b,1H), 5.38 (b, 1H), 6.56 (s, 1H), 7.03 (q, 4H).

EXAMPLE 47

N-[2,4-Bis(methylthio)-6-methylpyridin-3-yl]-N'-[(2-ethyl-2-phenyl)butyl]urea

A solution of 2-ethyl-2-phenylbutylamine (106 mg, 0.6 mmol) and 2,4-bis(methylthio)-6-methylpyridin-3-yl isocyanate (136 mg, 0.6 mmol) in 3 ml dimethylformamide was heated at 80° C. under nitrogen overnight. The reaction mixture was cooled to room temperature and diluted with 50 ml ethyl acetate. The resulting solution was washed sequentially with 3×25 ml water and 25 ml brine, dried (sodium sulfate), filtered and concentrated in vacuo. The residue was chromatographed on silica gel (125 g), eluting with 65:35 hexane/ethyl acetate to yield the title compound as a white solid (67 mg, 28% yield).

¹H NMR (300 MHz, CDCl₃) δ0.74 (t, 6H), 1.57–1.8 (c, 4H), 2.33 (s, 3H), 2.47 (s, 3H), 2.48 (s, 3H), 3.41 (d, 2H), 3.95 (b, 1H), 5.36 (b, 1H), 6.52 (s, 1H), 7.05–7.27 (c, 5H).

The urea derivatives of Examples 48–55 were prepared according to the method of Example 47.

EXAMPLE 48

N-[2,4-Bis(isoproylthio)-6-methylpyridin-3-yl]-N'-[(2-ethyl-2-phenyl)butyl]urea

35% yield.

¹H NMR (300 MHz, CDCl₃) δ0.72 (t, 6H), 1.29 (d, 6H), 1.33 (d, 6H), 1.57–1.8 (c, 4H), 2.45 (s, 3H), 3.39 (d and m, 3H), 3.93 (m and b, 2H), 5.28 (b, 1H), 6.58 (s, 1H), 7.04–7.2 (c, 5H).

EXAMPLE 49

N-[2,4-Bis (methylthio)-6-methylpyridin-3-yl]-N'-[(2-ethyl-2-{2-methylphenyl})butyl]urea 33% yield.

¹H NMR (300 MHz, CDCl₃) δ0.74 (t, 6H), 1.67 (m, 4H1), 2.28 (s, 3H), 2.33 (s, 3H), 2.47 (s, 3H), 2.49 (s, 3H), 3.4 (d, 2H), 3.97 (b, 1H), 5.35 (b, 1H), 6.53 (s, 1H), 6.94 (t, 1H), 6.98 (s, 2H), 7.08 (t, 1H).

EXAMPLE 50

N-[2,4-Bis(methylthiol-6-methylpyridin-3-yl]-N'-[(2-phenyl-2-propyl)pentyl]urea

88% yield.

¹H NMR (300 MHz, CDCl₃) δ0.85 (t, 6H), 0.88–1.3 (c, 4H), 1.59 (c, 4H), 2.32 (s, 3H), 2.47 (s, 3H), 2.49 (s, 3H), 3.4 (d, 2H), 3.96 (b, 1H), 5.33 (b, 1H), 6.52 (s, 1H), 7.05–7.24 (c, 5H).

EXAMPLE 51

N-[2,4-Bis(methylthio)-6-methylpyridin-3-yl]-N'-[(2-{2-methylphenyl}-2-propyl)pentyl]urea 43% yield.

¹H NMR (300 MHz, CDCl₃) δ0.84 (t, 6H), 0.961.3 (c, 4H), 1.58 (c, 4H), 2.27 (s, 3H), 2.32 (s, 3H), 2.46 (s, 3H), 2.47 (s, 3H), 3.39 (d, 2H), 3.96 (b, 1H), 5.3 (s, 1H), 6.52 (s, 1H), 6.93 (t, 1H), 6.97 (s, 2H), 7.06 (t, 1H).

EXAMPLE 52

N-[2,4-Bis(methylthio)-6-methylpyridin-3-yl]-N'-[(2-{2-methylphenyl}-2-butyl)hexyl]urea 57% yield.

¹H NMR (300 MHz, CDCl3) δ0.84 (t, 6H), 0.94–1.33 (c, 8H), 1.59 (c, 4H), 2.27 (s, 3H), 2.32 (s, 3H), 2.46 (s, 3H), 2.48 (s, 3H), 3.4 (d, 2H), 3.96 (b, 1H), 5.29 (s, 1H), 6.53 (s, 1H), 6.93 (c, 3H), 7.07 (t, 1H).

EXAMPLE 53

N-[2,4-Bis(methylthio)-6-methylpyridin-3-yl]-N'-[(2-{2,5-dimethoxyphenyl}-2-propyl)pentyl]urea 30% yield.

¹H NMR (300 MHz, CDCl₃) δ0.83 (t, 6H), 0.94–1.3 (c, 4H), 1.5–1.8 (c, 4H), 2.33 (s, 3H), 2.45 (s, 3H), 2.48 (s, 3H), 3.6 (d, 2H), 3.68 (s, 3H), 3.74 (s, 3H), 4.11 (b, 1h), 5.38 (b, 1H), 6.5 (s, 1H), 6.64 (s and m, total 3H).

EXAMPLE 54

N-[2,4-Bis(methylthio)-6-methylpyridin-3-yl]-N'-[(2-{2,3-dimethoxyphenyl}-2-propyl)pentyl]urea 45% yield.

¹H NMR (300 MHz, CDCl₃) δ0.83 (t, 6H), 0.98–1.25 (c, 4H), 1.67 (c, 4H), 2.32 (s, 3H), 2.44 (s, 3H), 2.47 (s, 3H), 3.59 (d, 2H), 3.78 (s, 3H), 3.82 (s, 3H), 4.08 (b, 1H), 5.33 (b, 1H), 6.51 (s, 1H), 6.66 (d, 1H), 6.77 (d, 1H), 6.84 (t, 1H).

EXAMPLE 55

N-2,4-Bis(methylthio)-6-methylpyridin-3-yl]-N'-[(2-{2,5-dimethylphenyl-}2-propyl)pentyl]urea 30% yield.

¹H NMR (300 MHz, CDCl₃) δ0.83 (t, 6H), 1.08 (m, 4H), 1.65 (c, 4H), 2.22 (s, 3H), 2.32 (s, 3H), 2.38 (s, 3H), 2.45 (s, 3H), 2.46 (s, 3H), 3.57 (d, 2H), 4.04 (b, 1H), 5.37 (b, 1H), 6.49 (s, 1H), 6.85 (c, 3H).

EXAMPLE 56

N-[2,4-Bis(methylthio)-6-methylpyridin-3-yl]-N'-[2-(2-methylphenyl)hexyl]urea

A solution of 2-(2-methylphenyl)hexylamine (153 mg, 0.8 mmol) and 2,4-bis(methylthio)-6-methylpyridin-3-yl isocyanate (180 mg, 0.8 mmol) in 3 ml dimethylformamide was heated at 80° C. under nitrogen overnight. The reaction mixture was cooled to room temperature and diluted with 60 ml ethyl acetate. The resulting solution was washed sequentially with 3×50 ml water and 50 ml brine, dried (sodium sulfate), filtered and concentrated in vacuo. The residue was chromatographed on silica gel (200 g), eluting with 7:3 hexane/ethyl acetate to yield the title compound as a white solid (110 mg, 33% yield).

$^1$H NMR (300 MHz, CDCl$_3$) δ0.80 (t, 3H), 1.06–1.32 (c, 4H), 1.46–1.74 (c, 2H), 2.23 (s, 3H), 2.30 (s, 3H), 2.43 (s, 3H), 2.48 (s, 3H), 3.03–3.26 (c, 2H), 3.51 (p, 1H), 4.21 (b, 1H), 5.33 (b, 1H), 6.52 (s, 1H), 7.01–7.11 (c, 4H).

The urea derivatives of Examples 57–82 were prepared according to the method of Example 56.

EXAMPLE 57

N-[2-(2-Methylphenyl)hexyl]-N'-[6-methylthioquinolin-5-yl]urea

28% yield.

$^1$H NMR (300 MHz, CDCl$_3$) δ0.80 (t, 3H) 0.98–1.28 (c, 4H), 1.4–1.65 (c, 2H), 2.08 (s, 3H), 2.48 (s, 3H), 2.96–3.27 (c, 2H), 3.51 (p, 1H), 4.10 (b, 1H), 5.94 (b, 1H), 6.87–7.02 (c, 4H), 7.36 (q, 1H), 7.57 (d, 1H), 8.06 (d, 1H), 8.14 (d, 1H), 8.82 (m, 1H).

EXAMPLE 58

N-[2,4-Bis(methylthio)-6-methylpyridin-3-yl]-N'-[2-(4-methylphenyl)heptyl]urea

24% yield.

$^1$H NMR (300 MHz, CDCl$_3$) δ0.80 (t, 3H), 1.07–1.28 (c, 6H), 1.45–1.7 (c, 2H), 2.28 (s, 3H), 2.32 (s, 3H), 2.45 (s, 3H), 2.48 (s, 3H), 2.65 (c, 1H), 3.10 (c, 1H), 3.56 (p, 1H), 4.21 (b, 1H), 5.35 (b, 1H), 6.54 (s, 1H), 6.98 (q, 4H).

EXAMPLE 59

N-[2-(4-Methylphenyl)heptyl]-N'-(6-methylthioquinolin-5-yl)urea

30% yield.

$^1$H NMR (300 MHz, CDCl$_3$) δ0.79 (t, 3H), 1.02–1.26 (c, 6H), 1.46–1.62 (c, 2H), 2.23 (s, 3H), 2.48 (s, 3H), 2.57 (c, 1H), 3.10 (c, 1H), 3.56 (p, 1H), 4.11 (b, 1H), 5.96 (s, 1H), 6.81 (q, 4H), 7.34 (q, 1H), 7.57 (d, 1H), 8.04 (d, 1H), 8.13 (d, 1H), 8.82 (m, 1H).

EXAMPLE 60

N-[2,4-Bis(methylthio)-6-methylpyridin-3-yl]-N'-[2-(3-methylphenyl)heptyl]urea

26% yield.

$^1$H NMR (300 MHz, CDCl$_3$) δ0.82 (t, 3H), 1.06–1.32 (c, 6H), 1.45–1.72 (c, 2H), 2.28 (s, 3H), 2.34 (s, 3H), 2.48 (s, 3H), 2.50 (s, 3H), 2.67 (c, 1H), 3.14 (m, 1H), 3.57 (p, 1H), 4.31 (b, 1H), 5.47 (b, 1H), 6.56 (s, 1H), 6.87 (d, 1H), 6.89 (s, 1H), 6,96 (d, 1H), 7.09 (t, 1H).

EXAMPLE 61

N-[2-(3-Methylphenyl)heptyl]-N'-(6-methylthioquinolin-5-yl)urea

24% yield.

$^1$H NMR (300 MHz, CDCl$_3$) δ0.8 (t, 3H) 1.0–1.3 (c, 6H), 1.37–1.64 (c, 2H), 2.19 (s, 3H), 2.48 (s, 3H), 2.59 (c, 1H), 3.14 (m, 1H), 3.57 (p, 1H), 4.23 (b, 1H), 6.11 (b, 1H), 6.7 (d, 1H), 6.72 (s, 1H), 6.88 (d, 1H), 6.97 (t, 1H), 7.35 (q, 1H), 7.56 (d, 1H), 8.04 (d, 1H), 8.14 (d, 1H), 8.81 (m, 1H).

EXAMPLE 62

N-[2-(3-Methylphenyl)heptyl]-N'-(6-methoxyguinolin-5-yl)urea

53% yield.

$^1$H NMR (300 MHz, CDCl$_3$) δ0.8 (t, 3H), 1.04–1.28 (c, 6H), 1.38–1.63 (c, 2H), 2.21 (s, 3H), 2.6 (m, 1H), 3.13 (m, 1H), 3.59 (m, 1H), 3.9 (s, 3H), 4.22 (b, 1H), 5.98 (b, 1H), 6.71 (d, 1H), 6.73 (s, 1H), 6.91 (d, $_1$H), 7.01 (t, 1H), 7.31 (q, 1H), 7.46 (d, 1H), 8.07 (d, 1H), 8.18 (d, 1H), 8.77 (m, 1H).

EXAMPLE 63

N-[2,4-Bis(methylthio)-6-methylpyridin-3-yl]-N'-[2-(2,5-dimethylphenyl)hexyl]urea 32% yield.

$^1$H NMR (300 MHz, CDCl$_3$) δ0.82 (t, 3H), 1.04–1.32 (c, 4H), 1.45–1.74 (c, 2H), 2.18 (s, 3H), 2.23 (s, 3H), 2.31 (s, 3H), 2.45 (s, 3H), 2.49 (s, 3H), 3.04 (m, 1H), 3.2 (m, 1H), 3.53 (p, 1H), 4.2 (b, 1H), 5.34 (b, 1H), 6.53 (s, 1H), 6.84 (d, 1H), 6.93 (d, 1H).

EXAMPLE 64

N-[2-(2,5-Dimethylphenyl)hexyl]-N'-(6-methylthioquinolin-5-yl)urea

33% yield.

$^1$H NMR (300 MHz, CDCl$_3$+DMSO-d$_6$) δ0.76 (t, 3H), 1.0–1.26 (c, 4H), 1.35–1.65 (c, 2H), 2.1 (s, 3H), 2.17 (s, 3H), 2.44 (s, 3H), 3.0 (c, 1H), 3.15 (m, 1H), 3.56 (p, 1H), 4.96 (b, 1H), 6.74–6.92 [total 4H, including 6.78 (d, 1H), 6.81 (s, 1H), 6.87 (d, 1H and b)], 7.34 (q, 1H), 7.56 (d, 1H), 8.02 (d, 1H), 8.16 (d, 1H), 8.76 (m, 1H).

EXAMPLE 65

N-[2-(2,5-Dimethylphenyl)hexyl]-N'-(6-methoxyguinolin-5-yl)urea

37% yield.

$^1$H NMR (300 MHz, CDCl$_3$+DMSO-d$_6$) δ0.76 (t, 3H), 1.0–1.28 (c, 4H), 1.35-1.65 (c, 2H), 2.07 (s, 3H), 2.17 (s, 3H), 3.0 (c, 1H), 3.11 (m, 1H), 3.57 (p, 1H), 3.86 (s, 3H), 4.71 (b, $_1$H), 6.46 (b, 1H), 6.77 (s, 1H), 6.78 (d, 1H), 6.86 (d, 1H), 7.28 (q, 1H), 7.42 (d, 1H), 8.0 (d, 1H), 8.16 (d, 1H), 8.71 (m, 1H).

EXAMPLE 66

N-[2,4-Bis(methylthio)-6-methylpyridin-3yl-N'-[2-(2,5dimethylphenyl)heptyl]urea

28% yield.

$^1$H NMR (300 MHz, CDCl$_3$) δ0.82 (t, 3H), 1.08–1.3 (c, 6H), 1.43–1.74 (c, 2H), 2.19 (s, 3H), 2.23 (s, 3H), 2.33 (s,

3H), 2.48 (s, 3H), 2.53 (s, 3H), 3.04 (c, 1H), 3.21 (m, 1H), 3.51 (p, 1H), 4.35 (b, 1H), 5.0 (b, 1H), 6.56 (s, 1H), 6.84 (d, 1H), 6.86 (d, 1H), 6.93 (d, 1H).

EXAMPLE 67

N-[2,4-Bis(methylthio)-6methylpyridin-3-yl]-N'-[2-(2,4-dimethylphenyl)hexyl]urea 68% yield.

$^1$H NMR (300 MHz, CDCl$_3$) δ0.81 (t, 3H), 1.05–1.31 (c, 4H), 1.42–1.75 (c, 2H), 2.2 (s, 3H), 2.26 (s, 3H), 2.32 (s, 3H), 2.46 (s, 3H), 2.52 (s, 3H), 3.04 (c, 1H), 3.18 (m, 1H), 3.49 (p, 1H), 4.3 (b, 1H), 5.46 (b, 1H), 6.55 (s, 1H), 6.86 (s, 1H), 6.89 (d, 1H), 6.95 (d, 1H).

EXAMPLE 68

N-[2,4-Bis(methylthio)-6-methylpyridin-3-yl]-N'-[2-(3-methylphenyl)hexyl]urea

60% yield.

$^1$H NMR (300 MHz, CDCl$_3$) δ0.81 (t, 3H), 1.05–1.33 (c, 4H), 1.45–1.75 (c, 2H), 2.28 (s, 3H), 2.34 (s, 3H), 2.49 (s, 3H), 2.51 (s, 3H), 2.67 (m, 1H), 3.15 (m, 1H), 3.57 (p, 1H), 4.34 (b, 1H), 5.48 (b, 1H), 6.57 (s, 1H), 6.88 (d, 1H), 6.89 (s, 1H), 6.96 (d, 1H), 7.1 (t, 1H).

EXAMPLE 69

N-[2,4-Bis(methylthio)-6-methylpyridin-3-yl]-N'-[2-(2,4-dimethylphenyl)heptyl]urea 59% yield.

$^1$H NMR (300 MHz, CDCl$_3$) δ0.81 (t, 3H), 1.08–1.28 (c, 6H), 1.42–1.72 (c, 2H), 2.19 (s, 3H), 2.26 (s, 3H), 2.32 (s, 3H), 2.45 (s, 3H), 2.51 (s, 3H), 3.04 (c, 1H), 3.18 (m, 1H), 3.49 (p, 1H), 4.24 (b, 1H), 5.38 (b, 1H), 6.55 (s, 1H), 6.86 (s, 1H), 6.89 (d, 1H), 6.95 (d, 1H).

EXAMPLE 70

N-[2,4-Bis(methylthio)-6-methylpyridin-3-yl]-N'-[2-(naphth-1-yl)heptyl]urea

50% yield.

$^1$H NMR (300 MHz, CDCl$_3$) δ0.79 (t, 3H), 1.14–1.34 (c, 6H), 1.56–1.92 (c, 2H), 2.14 (s, 3H), 2.38 (s, 3H), 2.44 (s, 3H), 3.48 (m, 1H), 3.6 (p, 1H), 3.73 (c, 1H), 4.26 (b, 1H), 5.37 (b, 1H), 6.39 (s, 1H), 7.28 (d, 1H), 7.36 (t, 1H), 7.47 (c, 2H), 7.67 (d, 1H), 7.82 (c, 1H), 8.13 (c, 1H).

EXAMPLE 71

N-[2,4-Bis(methylthio)-6-methylpyridin-3-yl]-N'-[2-(naphth-2-yl)hexyl]urea

36% yield.

$^1$H NMR (300 MHz, CDCl$_3$) δ0.8 (t, 3H), 1.06–1.35 (c, 4H), 1.55–1.81 (c, 2H), 2.07 (s, 3H), 2.37 (s, 3H), 2.4 (s, 3H), 2.9 (c, 1H), 3.24 (m, 1H), 3.66 (p, 1H), 4.25 (b, 1H), 5.39 (b, 1H), 6.34 (s, 1H), 7.25 (m, 1H), 7.4-7.51 (c, 3H), 7.68–7.87 (c, 3H).

EXAMPLE 72

N-[2,4-Bis(methylthio)-6-methylpyridin-3-yl]-N'-[2-(naphth-1 -yl)hexyl]urea

36% yield.

$^1$H NMR (300 MHz, CDCl$_3$) δ0.79 (t, 3H), 1.1–1.34 (c, 4H), 1.56–1.92 (c, 2H), 2.13 (s, 3H), 2.37 (s, 3H), 2.44 (s, 3H), 3.47 (m, 1H), 3.6 (p, 1H), 3.73 (c, 1H), 4.28 (b, 1H), 5.36 (b, 1H), 6.4 (s, 1H), 7.28 (d, 1H), 7.35 (t, 1H), 7.46 (c, 2H), 7.66 (d, 1H), 7.82 (c, 1H), 8.12 (c, 1H).

EXAMPLE 73

N-(6-Methylthioquinolin-5-yl)-N'-[2-(naphth-1-yl)hexyl]urea

34% yield.

$^1$H NMR (300 MHz, CDCl$_3$) δ0.78 (t, 3H), 1.1–1.3 (c, 4H), 1.56–1.82 (c, 2H), 2.35 (s, 3H), 3.44 (c, 1H), 3.7 (c, 2H), 4.21 (b, 1H), 5.98 (s, 1H), 7.08 (c, 2H), 7.22 (t, 1H), 7.42 (c, 3H), 7.6 (d, 1H), 7.8 (d, 1H), 7.9 (d, 1H), 7.94 (d, 1H), 8.03 (d, 1H), 8.7 (m, 1H),

EXAMPLE 74

N-[2,4-Bis(methylthio)-6-methylpyridin-3-yl]-N'-[2-(2,3-dimethoxyphenyl)heptyl]urea 29% yield.

$^1$H NMR (300 MHz, CDCl$_3$) δ0.81 (t, 3H), 1.1–1.3 (c, 6H), 1.45–1.77 (c, 2H), 2.33 (s, 3H), 2.48 (s, 3H), 2.53 (s, 3H), 3.12–3.35 (c, 2H), 3.45 (p, 1H), 3.69 (s, 3H), 3.84 (s, 3H), 4.54 (b, 1H), 5.52 (b, 1H), 6.59 (s, 1H), 6.7 (d, 1H), 6.73 (d, 1H), 6.95 (t, 1H).

EXAMPLE 75

N-[2-(2,3-Dimethoxaphenyl)heptyl]-N'-(6-methylthioquinolin-5-yl)urea

31% yield.

$^1$H NMR (300 MHz, CDCl$_3$) δ0.81 (t, 3H), 1.05–1.3 (c, 6H), 1.42–1.65 (c, 2H), 2.49 (s, 3H), 3.12 (c, 1H), 3.27 (c, 1H), 3.46 (m, 1H), 3.53 (s, 3H), 3.8 (s, 3H), 4.44 (b, 1H), 6.04 (b, 1H), 6.56 (d, 1H), 6.66 (d, 1H), 6.85 (t, 1H), 7.37 (q, 1H), 7.61 (d, 1H), 8.08 (d, 1H), 8.17 (d, 1H), 8.82 (m, 1H).

EXAMPLE 76

N-[2,4-Bis(methylthio)-6-methylpyridin-3-yl]-N'-[2-(3-methylphenyl)octyl]urea

47% yield.

$^1$H NMR (300 MHz, CDCl$_3$) δ0.83 (t, 3H), 1.19 (b, 8H), 1.46–1.72 (c, 2H), 2.27 (s, 3H), 2.33 (s, 3H), 2.46 (s, 3H), 2.48 (s, 3H), 2.66 (c, 1H), 3.13 (c, 1H), 3.58 (p, 1H), 4.23 (b, 1H), 5.35 (s, 1H), 6.55 (s, 1H), 6.87 (d) and 6.88 (s) (total 2H), 6.96 (d, 1H), 7.09 (t, 1H).

EXAMPLE 77

N-[2-(3-Methylphenyl)octyl]-N'-(6-methoxyguinolin-5-yl)urea

54% yield.

$^1$H NMR (300 MHz, CDCl$_3$) δ0.83 (t, 3H), 1.18 (b, 8H), 1.53 (c, 2H), 2.22 (s, 3H), 2.61 (m, 1H), 3.14 (m, 1H), 3.6 (p, 1H), 3.91 (s, 3H), 4.24 (b, 1H), 5.99 (s, 1H), 6.72 (d) and 6.73 (s) (total 2H), 6.92 (d, 1H), 7.01 (t, 1H), 7.33 (q, 1H), 7.47 (d, 1H), 8.09 (d, 1H), 8.19 (d, 1H), 8.77 (q, 1H).

EXAMPLE 78

N-[2-(3-Methylphenyl)octyl]-N'-(6-methylthioquinolin-5-yl)urea

25% yield.

¹H NMR (300 MHz, CDCl₃) δ0.83 (t, 3H), 1.17 (b, 8H), 1.52 (c, 2H), 2.2 (s, 3H), 2.49 (s, 3H), 2.6 (m, 1H), 3.15 (m, 1H), 3.58 (p, 1H), 4.21 (b, 1H), 6.05 (s, 1H), 6.71 (d) and 6.73 (s) (total 2H), 6.89 (d, 1H), 6.99 (t, 1H), 7.37 (q,1H), 7.58 (d, 1H), 8.07 (d, 1H) 8.17 (d, 1H), 8.82 (t, 1H).

EXAMPLE 79

N-[2-(naphth-1-yl)heptyl]-N'-(6-methoxyguinolin-5-yl)urea

58% yield.

¹H NMR (300 MHz, CDCl₃) δ0.81 (t, 3H), 1.19 (b, 6H), 1.7 (b, 2H), 3.41 (c, 1H), 3.72 (c) and 3.75 (s) (total 5H), 4.21 (b, 1H), 5.88 (s, 1H), 7.02 (q, 1H), 7.13 (d, 1H) 7.25 (t, 1H), 7.33 (d, 1H), 7.45 (m, 2H), 7.63 (d, 1H), 7.83 (d, 1H), 7.92 (d, 1H), 7.98 (d, 1H), 8.04 (d, 1H), 8.65 (m, 1H).

EXAMPLE 80

N-[2-(naphth-1-yl)heptyl]-N'-(6-methylthioquinolin-5-yl)urea

47% yield.

¹H NMR (300 MHz, CDCl₃) δ0.81 (t, 3H), 1.17 (b, 6H), 1.7 (b, 2H), 2.35 (s, 3H), 3.44 (c, 1H), 3.6–3.78 (c, 2H), 4.22 (b, 1H), 5.97 (s, 1H), 7.06 (q, 1H), 7.12 (d, 1H), 7.23 (t, 1H), 7.43 (m, 3H), 7.6 (d, 1H), 7.81 (d, 1H), 7.9 (d, 1H), 7.96 (d, 1H), 8.03 (d, 1H), 8.69 (m, 1H).

EXAMPLE 81

N-[2-(2,4-Dimethylphenyl)heptyl]-N'-(6-methylthioquinolin-5-yl)urea

41% yield.

¹H NMR (300 MHz, CDCl₃) δ0.79 (t, 3H), 1.14 (b, 6H), 1.48 (c, 2H), 2.0 (s, 3H), 2.2 (s, 3H), 2.47 (s, 3H), 2.95 (c, 1H), 3.15 (m, 1H), 3.5 (p, 1H), 4.06 (b, 1H), 5.91 (s, 1H), 6.71 (s, 1H), 6.75 (s, 2H), 7.32 (q, 1H), 7.55 (d, 1H), 8.03 (d, 1H), 8.03 (d, 1H), 8.11 (d, 1H), 8.82 (q, 1H).

EXAMPLE 82

N-[2-(2,4-Dimethylphenyl)heptyl]-N'-(6-methoxyquinolin-5-yl)urea

57% yield.

¹H NMR (300 MHz, CDCl₃) δ0.8 (t, 3H), 1.16 (b, 6H), 1.49 (c, 2H), 2.02 (s, 3H), 2.23 (s, 3H), 2.97 (c, 1H), 3.13 (m, 1H), 3.55 (p, 1H), 3.9 (s, 3H), 4.14 (b, 1H), 5.89 (s, 1H), 6.75 (s, 1H), 6.78 (s, 2H), 7.28 (q, 1H), 7.44 (d, 1H), 8.04 (d, 1H), 8.14 (d, 1H), 8.77 (q, 1H).

EXAMPLE 83

N-[2,4-Bis(methyl)-6-methylpyridin-3-yl]-N'-[2-(3,4,5-trimethoxyphenyl)heptyl]urea 45% yield.

¹H NMR (300 MHz, CDCl₃) δ0.83 (t, 3H), 1.23 (b, 6H), 1.4–1.7 (c, 2H), 2.3 (s, 3H), 2.45 (s, 3H), 2.48 (s, 3H), 2.64 (c, 1H), 3.12 (m, 1H), 3.57 (q, 1H), 3.79 (s, 6H), 3.82 (s, 3H), 4.23 (b, 1H), 5.39 (b, 1H), 6.27 (s, 2H), 6.54 (s, 1H).

EXAMPLE 84

N-[2,4-Bis(methylthio)-6-methylpyridin-3-yl]-N'-[2-(2,5-dimethyl-4-methoxyphenyl)heptyl]urea 35% yield.

¹H NMR (300 MHz, CDCl₃) δ0.82 (t, 3H), 1.19 (b, 6H), 1.5 (c, 1H), 1.63 (c, 1H), 2.11 (s, 3H), 2.2 (s, 3H), 2.34 (s, 3H), 2.49 (s, 3H), 2.54 (s, 3H), 2.98 (c, 1H), 3.18 (m, 1H), 3.49 (p, 1H), 3.79 (s, 3H), 4.2 (b, 1H), 5.35 (b, 1H), 6.5 (s, 1H), 6.58 (s, 1H), 6.79 (s, 1H).

EXAMPLE 85

N-[2,4-Bis(methylthio)-6-methylpyridin-3-yl]-N'-[2-(2,5-dimethoxyphenyl)heptyl]urea 40% yield.

¹H NMR (300 MHz, CDCl₃) δ0.82 (t, 3H), 1.2 (b, 6H), 1.63 (b, 2H), 2.34 (s, 3H), 2.46 (s, 3H), 2.51 (s, 3H), 3.15 (c, 1H), 3.26–3.5 (c, 2H), 3.62 (s, 3H), 3.73 (s, 3H), 4.48 (b, 1H), 5.54 (b, 1H), 6.58 (s, 1H), 6.61–6.71 (c, 3H).

EXAMPLE 86

N-2-(2,5-Dimethoxyphenyl)heptyl]-N'-(6-methylthioquinolin-5-yl)urea

30% yield.

¹H NMR (300 MHz, CDCl₃) δ0.81 (t, 3H), 1.17 (b, 6H), 1.54 (b, 2H), 2.49 (s, 3H), 3.08 (c, 1H), 3.24–3.4 (m including s at 3.38, total 4H), 3.45 (p, 1H), 3.72 (s, 3H), 4.42 (b, 1H), 6.05 (b, 1H), 6.49 (d, 1H), 6.52–6.61 (c, 2H), 7.35 (q, 1H), 7.61 (d, 1H), 8.09 (d, 1H), 8.14 (d, 1H), 8.81 (m, 1H).

EXAMPLE 87

N-[2-(2,5-Dimethoxyphenyl)heptyl-N'-(6-methoxyquinolin-5-yl)urea

39% yield.

¹H NMR (300 MHz, CDCl₃) δ0.81 (t, 3H), 1.18 (b, 6H), 1.55 (b, 2H), 3.09 (c, 1H), 3.27 (m, 1H), 3.37 (s, 3H), 3.49 (p, 1H), 3.72 (s, 3H), 3.9 (s, 3H), 4.45 (b, 1H), 5.98 (b, 1H), 6.51 (d, 1H), 6.55–6.63 (c, 2H), 7.31 (q, 1H), 7.48 (d, 1H), 8.09 (d, 1H), 8.17 (d, 1H), 8.77 (q, 1H).

EXAMPLE 88

N-[2,4-Bis(methylthio)-6-methylpyridin-3-yl]-N'-[2-(3,5-dimethoxyphenyl)heptyl]urea 45% yield.

¹H NMR (300 MHz, CDCl₃) δ0.82 (t, 3H), 1.2 (b, 6H), 1.44–1.68 (c, 2H), 2.33 (s, 3H), 2.44 (s, 3H), 2.47 (s, 3H), 2.65 (c, 1H), 3.11 (m, 1H), 3.58 (p, 1H), 3.74 (s, 6H), 4.22 (b, 1H), 5.34 (s, 1H), 6.24 (s and c, 3H), 6.54 (s, 1H).

EXAMPLE 89

N-[2,4-Bis(methylthio)-6-methylpyridin-3-yl]-N'-[2-(2,5-dimethoxyphenyl)octyl]urea 50% yield.

¹H NMR (300 MHz, CDCl₃) δ0.83 (t, 3H), 1.2 (b, 8H), 1.64 (b, 2H), 2.33 (s, 3H), 2.45 (s, 3H), 2.5 (s, 3H), 3.15 (c, 1H), 3.27–3.5 (c, 2H), 3.61 (s, 3H), 3.73 (s, 3H), 4.43 (b, 1H), 5.47 (b, 1H), 6.57 (s, 1H), 6.6–6.71 (c, 3H).

EXAMPLE 90

N-[2,4-Bis(methylthio)-6-methylpyridin-3-yl]-N'-2-[2-(3-methylphenyl)-6,6,6-trifluorohexyl]urea 34% yield.

¹H NMR (300 MHz, CDCl₃) δ1.42 (c, 2H), 1.55–1.82 (c, 2H), 2.0 (c, 2H), 2.28 (s, 3H), 2.34 (s, 3H), 2.47 (s, 3H), 2.48 (s, 3H), 2.68 (c, 1H), 3.17 (m, 1H), 3.56 (p, 1H), 4.28 (b, 1H), 5.39 (s, 1H), 6.56 (s, 1H), 6.88 (d) and 6.89 (s) (total 2H), 6.98 (d, 1H), 7.12 (t, 1H).

EXAMPLE 91

N-[2-(3-Methylphenyl)heptyl]-N'-(6-pentylthioquinolin-5-yl)urea

53% yield.

¹H NMR (300 MHz, CDCl₃) δ0.81 (t, 3H), 0.9 (t, 3H), 1.04–1.7 (c, 14H), 2.2 (s, 3H), 2.59 (c, 1H), 2.93 (t, 2H), 3.14 (m, 1H), 3.59 (p, 1H), 4.15 (b, 1H), 6.11 (s, 1H), 6.69 (d) and 6.71 (s) (total 2H), 6.89 (d, 1H), 6.99 (t, 1H), 7.33 (q, 1H), 7.62 (d, 1H), 7.98 (d, 1H), 8.13 (d, 1H), 8.82 (q, 1H).

EXAMPLE 92

N-[2,4-Bis(methylthio)-6-methylpyridin-3-yl]-N'-{2,-(5chlorobenzo[b]thiophen-3-yl)heptyl}urea 36% yield.

¹H NMR (300 MHz, CDCl₃) δ0.82 (t, 3H), 1.22 (b, 6H), 1.63 (b, 2H), 2.23 (s, 3H), 2.4 (s, 3H), 2.46 (s, 3H), 3.21 (m, 1H), 3.51 (c, 2H), 4.32 (b, 1H), 5.44 (b, 1H), 6.48 (s, 1H), 7.13 (s, 1H), 7.29 (c, 1H), 7.72 (d, 1H), 7.41 (s, 1H).

EXAMPLE 93

N-[2,4-Bis(methylthio)-6-methylpyridin-3-yl]-N'-[2-(3,5dimethylphenyl)heptyl]urea 34% yield.

¹H NMR (300 MHz, CDCl₃) δ0.82 (t, 3H), 1.21 (b, 6H), 1.57 (b, 2H), 2.23 (s, 6H), 2.33 (s, 3H), 2.46 (s, 3H), 2.48 (s, 3H), 2.61 (c, 1H), 3.13 (m, 1H), 3.56 (p, 1H), 4.21 (b, 1H), 5.33 (s, 1H), 6.55 (s, 1H), 6.67 (s, 2H), 6.78 (s, 1H).

EXAMPLE 94

N-[2,4-Bis(methylthio)-6-methylpyridin-3-yl]-N'-[2-(2,5-dimethylphenyl)octyl]urea 35% yield.

¹H NMR (300 MHz, CDCl₃) δ0.84 (t, 3H), 1.19 (b, 8H), 1.6 (b, 2H), 2.18 (s, 3H), 2.23 (s, 3H), 2.31 (s, 3H), 2,45 (s, 3H), 2,49 (s, 3H), 3.04 (c, 1H), 3.2 (m, 1H), 3.52 (p, 1H), 4.22 (b, 1H), 5.37 (b, 1H), 6.54 (s, 1H), 6.84 (d) and 6.85 (s), (total 2H), 6.92 (d, 1H).

EXAMPLE 95

N-[2,4-Bis(methylthio)-6-methylpyridin-3-yl]-N'-[5-methyl-2-{3-methylphenyl}hexyl]urea 44% yield.

¹H NMR (300 MHz, CDCl₃) δ0.79, 0.8, 0.81, 0.82 (2d, 6H), 0.92–1.18 (c, 2H), 1.38–1.74 (c, 3H), 2.28 (s, 3H), 2.33 (s, 3H), 2.46 (s, 3H), 2.48 (s, 3H), 2.63 (c, 1H), 3.14 (m, 1H), 3.58 (p, 1H), 4.22 (b, 1H), 5.36 (s, 1H), 6.55 (s, 1H), 6.87 (d) and 6.68 (s) (total 2H), 6.96 (d, 1H), 7.09 (t, 1H).

EXAMPLE 96

N-[2,4-Bis(methylthio)-6-methylpyridin-3-yl]-N'-[2-{2,5-dimethylphenyl}-4-phenylbutyl]urea 33% yield.

¹H NMR (300 MHz, CDCl₃) δ1.8–1.96 (m, 1H), 1.99–2.14 (m) and 2.11 (s) (total 4H), 2.24 (s, 3H), 2.3 (s, 3H), 2.4–2.54 (m, 8H) including 2.44 (s, 3H) and 2.49 (s, 3H), 3.08 (c, 1H), 3.3 (m, 1H), 3.49 (p, 1H), 4.25 (b, 1H), 5.37 (s, 1H), 6.54 (s, 1H), 6.87 (d) and (6.9 (s) (total 2H), 6.95 (d, 1H), 7.08 (d) and 7.09 (s) (total 2H), 7.14 (m, 1H), 7.23 (m, 2H).

EXAMPLE 97

N-[2,4-Bis(methylthio)-6-methylpyridin-3-yl]-N'-[2-(2,5-dimethylphenyl)-5-phenylpentyl]urea 19% yield.

¹H NMR (300 MHz, CDCl₃) δ1.4–1.8 (c, 4H), 2.17 (s, 3H), 2.22 (s, 3H), 2.3 (s, 3H), 2.43 (s, 3H), 2.48 (s, 3H), 2.53 (c, 2H), 3.08 (c, 1H), 3.2 (m, 1H), 3.52 (p, 1H), 4.22 (b, 1H), 5.36 (s, 1H), 6.52 (s, 1H), 6.81 (s) and 6.83 (d) (total 2H), 6.91 (d, 1H), 7.08 (d, 2H), 7.13 (m, 1H), 7.23 (m, 2H).

EXAMPLE 98

N-[2,4-Bis(methylthio)-6-methylpyridin-3-yl-N'-[2-(naphth-1-yl)-6-methylheptyl]urea 59% yield.

¹H NMR (300 MHz, CDCl₃) δ0.76 (t, 6H), 1.06–1.34 (c, m, 4H), 1.43 (h, 1H), 1.75 (c, 2H), 2.13 (s, 3H), 2.37 (s, 3H), 2.43 (s, 3H), 3.48 (m, 1H), 3.56–3.82 (c, 2H), 4.21 (c, 1H), 5.28 (s, 1H), 6.37 (s, 1H), 7.28 (m, 1H), 7.36 (t, 1H), 7.46 (m, 2H), 7.67 (d, 1H), 7.83 (m, 1H), 8.13 (m, 1H).

EXAMPLE 99

N-[2,4-Bis(ethylthio)-methylpyridin-3-yl]-N'-[2-(naphth-1-yl)-6-methylheptyl]urea 31% yield.

¹H NMR (300 MHz, CDCl₃) δ0.74, 0.76, 0.79 (2d, 6H), 1.06–1.32 (m, c, 10H), 1.42 (h, 1H), 1.78 (c, 2H), 2.42 (s, 3H), 2.68 (q, 2H), 3.02 (q, 2H), 3.53 (m, 2H), 3.72 (c, 1H), 4.20 (c, 1H), 5.27 (s, 1H), 6.42 (s, 1H), 7.28 (m, 1H), 7.34 (t, 1H), 7.46 (m, 2H), 7.67 (d, 1H), 7.81 (m, 1H), 8.12 (m, 1H).

EXAMPLE 100

N-[2,4-Bis(ethylthio)-6-methylpyridin-3-yl]-N'-[2-(2,5-dimethylphenyl)-6-methylheptyl]urea 38% yield.

¹H NMR (300 MHz, CDCl₃) δ0.77, 0.79, 0.81 (2d, 6H), 1.04–1.72 [c, m including 2t (1.29, 1.31, 6H), total 13H], 2.18 (s, 3H), 2.22 (s, 3H), 2.46 (s, 3H), 2.81 (q, 2H), 2.98–3.25 [m including q (3.08, 2H), total 4H], 3.53 (p, 1H), 4.2 (c, 1H), 5.32 (s, 1H), 5.56 (s, 1H), 6.84 (d, 1H), 6.92 (d, 1H), 7.26 (s, 1H).

EXAMPLE 101

N-[2,4-Bis(ethylthio)-6-methylpyridin-3-yl]-N'-[2-(naphth-1-yl)heptyl]urea

15% yield.

¹H NMR (300 MHz, CDCl₃) δ0.79 (t, 3H), 1.23 (m, c, 12H), 1.65–1.94 (c, 2H), 2.42 (s, 3H), 2.68 (q, 2H), 3.02 (q, 2H), 3.54 (c, 2H), 3.72 (c, 1H), 4.22 (c, 1H), 5.28 (s, 1H), 6.42 (s, 1H), 7.32 (m, 2H), 7.45 (m, 2H), 7.67 (d, 1H), 7.82 (m, 1H), 8.11 (m, 1H).

EXAMPLE 102

N-[2,4-Bis(ethylthio)-6-methylpyridin-3-yl]-N'-[2-(2,5-dimethylphenyl)-6-phenylhexyl]urea 57% yield.

$^1$H NMR (300 MHz, CDCl$_3$) δ1.14–1.36 [c including 2t (1.28, 1.3, 6H), total 10H], 1.48–1.8 (m, c, 4H), 2.17 (s, 3H), 2.23 (s, 3H), 2.46 (s, 3H), 2.52 (t, 2H), 2.81 (q, 2H), 2.29–3.13 [c and q (3.07, 2H) total 3H], 3.2 (m, 1H), 3.52 (p, 1H), 4.21 (c, 1H), 5.33 (s, 1H), 6.56 (s, 1H), 6.85 (d, 1H), 6.93 (d, 1H), 7.13 (m, 3H), 7.24 (m, 3H).

EXAMPLE 103

N-[2,4-Bis(ethylthio)-6-methylpyridin-3-yl]-N'-[2-(2,5-dimethylphenyl)heptyl]urea 48% yield.

$^1$H NMR (300 MHz, CDCl$_3$) δ0.82 (t, 3H), 1.2 (c, 6H), 1.29, 1.31 (2t, 6H), 1.47 –1.72 (c, 2H), 2.17 (s, 3H), 2.23 (s, 3H), 2.46 (s, 3H), 2.82 (q, 2H), 2.98–3.13 [c including q (3.08), total 3H], 3.19 (m, 1H), 3.53 (p, 1H), 4.18 (b, 1H), 5.29 (s, 1H), 6.56 (s, 1H), 6.84 (d) and 6.85 (s), total 2H, 6.92 (d, 1H).

EXAMPLE 104

N-[2,4-Bis(methylthio)-6-methylpyridin-3-yl]-N'-[2-(2,4,6-trimethylphenyl)octyl]urea 27% yield.

$^1$H NMR (300 MHz, CDCl$_3$) δ0.83 (t, 3H), 1.2 (c, 8H), 1.7 (c, 2H), 2.16 (s, 3H), 2.22 (s, 3H), 2.28 (s, 3H), 2.3 (s, 3H), 2.42 (s, 3H), 2.48 (s, 3H), 3.28 (c, 2H), 3.68 (m, 1H), 4.14 (b, 1H), 5.29 (s, 1H), 6.48 (s, 1H), 6.66 (s, 1H), 6.69 (s, 1H).

EXAMPLE 105

N-[2,4-Bis(ethylthio)-6-methylpyridin-3-yl]-N'-[2-(2,5-dimethylphenyl)-6,6,6-trifluorohexyl]urea 20% yield.

$^1$H NMR (300 MHz, CDCl$_3$) δ1.29,1.32 (2t, 6H), 1.43 (c, 2H), 1.63 (c, 1H), 1.78 (c, 1H), 2.0 (c, 2H), 2.2 (s, 3H), 2.24 (s, 3H), 2.46 (s, 3H), 2.84 (q, 2H), 3.0–3.15 [c including t (3.09) total 3H], 3.22 (m, 1H), 3.49 (p, 1H), 4.25 (b, 1H), 5.34 (s, 1H), 6.58 (s, 1H), 6.86 (d, 2H), 6.95 (d, 1H).

EXAMPLE 106

N-[2,4-Bis(methylthio)-6-methylpyridin-3-yl]-N'-[2-(5-methylbenzo[b]thiophen-3-yl)heptyl]urea 10% yield.

$^1$H NMR (300 MHz, CDCl$_3$) δ0.82 (c, 3H), 1.24 (c, 6H), 1.74 (c, 2H), 2.2 (s, 3H), 2.4 (s, 3H), 2.46 (s, 6H), 3.25 (m, 1H), 3.5 (t, 2H), 4.28 (b, 1H), 5.37 (s, 1H), 6.45 (s, 1H), 6.99 (s, 1H), 7.15 (d, 1H), 7.55 (s, 1H), 7.71 (d, 1H).

EXAMPLE 107

N-[2,4-Bis(methylthio-6-methylpyridin-3-yl]-N'-[2-(2-chlorobenzo[b]thiophen-3-yl)heptyl]urea 32% yield.

$^1$H NMR (300 MHz, CDCl$_3$) δ0.79 (c, 3H), 1.2 (c, 6H), 1.79 (c, 1H), 1.91 (c, 1H), 2.23 (s, 3H), 2.37 (s, 3H), 2.46 (s, 3H), 3.4–3.59 (c, 2H), 3.79 (c, 1H), 4.27 (b, 1H), 5.36 (s, 1H), 6.47 (s, 1H), 7.3 (m, 2H), 7.67 (m, 1H), 7.76 (c, 1H).

EXAMPLE 108

N-[2-(2,5-Dimethylphenyl)heptyl]-N'-[6-methylthioquinolin-5-yl]urea

33% yield.

$^1$H NMR (300 MHz, CDCl$_3$) δ0.82 (t, 3H), 1.16 (c, 6H), 1.5 (c, 2H), 2.0 (s, 3H), 2.13 (s, 3H), 2.47 (s, 3H), 2.96 (m, 1H), 3.16 (m, 1H), 3.55 (p, 1H), 4.09 (b, 1H), 5.97 (s, 1H), 6.7 (s, 1H), 6.77 (q, 2H), 7.34 (q, 1H), 7.56 (d, 1H), 8.03 (d, 1H), 8.2 (d, 1H), 8.82 (q, 1H).

EXAMPLE 109

N-[2,4-Bis(methylthio)-6-methylpyridin-3-yl]-N-[2-(2,5-dimethylphenyl)-6-methylheptyl]urea 35% yield.

$^1$H NMR (300 MHz, CDCl$_3$) δ0.77, 0.79, 0.81 (2d, 6H), 1.04–1.7 (c, 7H), 2.18 (s, 3H), 2.23 (s, 3H), 2.31 (s, 3H), 2.44 (s, 3H), 2.48 (s, 3H), 3.04 (c, 1H), 3.19 (m, 1H), 3.53 (p, 1H), 4.2 (b, 1H), 5.33 (s, 1H), 6.53 (s, 1H), 6.84 (d and s, 2H), 6.92 (d, 1H).

EXAMPLE 110

N-[2,4-Bis(ethylthio)-6-methylpyridin-3-yl]-N'-[2-(2,5-dimethylphenyl)-5-phenylpentyl]urea 37% yield.

$^1$H NMR (300 MHz, CDCl$_3$) δ1.26, 1.29, 1.31, 1.33 (2t, 6H), 1.41–1.82 (c, 4H), 2.17 (s, 3H), 2.22 (s, 3H), 2.46 (s, 3H), 2.54 (c, 2H), 2.81 (q, 2H), 3.0–3.24 [c and including q (3.08), total 4H], 3.52 (p, 1H), 4.2 (b, 1H), 5.31 (s, 1H), 6.56 (s, 2H), 6.82 6.85 (s and d, 2H), 6.91 (d, 1H), 7.08 (d, 2H), 7.15 (d, 1H), 7.23 (t, 2H).

EXAMPLE 111

N-[2,4-Bis(ethylthio)-6-methylpyridin-3-yl]-N'-[2-(2,5-dimethylphenyl)octyl]urea 26% yield.

$^1$H NMR (300 MHz, CDCl$_3$) δ0.83 (t, 3H), 1.19 (c, 8H), 1.27, 1.29, 1.32, 1.34 (2t, 6H), 1.54 (c, 1H), 1.67 (c, 1H), 2.18 (s, 3H), 2.23 (s, 3H), 2.46 (s, 3H), 2.82 (q, 2H), 2.98–3.14 [c including t (3.08) total 3H], 3.19 (m, 1H), 3.53 (p, 1H), 4.2 (b, 1H), 5.31 (s, 1H), 6.56 (s, 1H), 6.83, 6.85 (s and d, 2H), 6.92 (d, 1H).

EXAMPLE 112

N-[2,4-Bis(ethylthio)-6-methylpyridin-3-yl]-N'-[2-(2,5-dimethylphenyl)-5-methylhexyl]urea 39% yield.

$^1$H NMR (300 MHz, CDCl$_3$) δ0.79, 0.80, 0.81, 0.82 (2d, 6H), 0.92–1.18 (c, 2H), 1.27, 1.29, 1.31, 1.34 (2t, 6H), 1.4–1.75 (c, 3H), 2.17 (s, 3H), 2.23 (s, 3H), 2.46 (s, 3H), 2.82 (q, 2H), 2.93–3.13 [c including t (3.08), total 3H], 3.2 (m, 1H), 3.53 (p, 1H), 4.2 (b, 1H), 5.3 (s, 1H), 6.56 (s, 1H), 6.83, 6.85 (d and s, 2H), 6.92 (d, 1H).

EXAMPLE 113

N-[2,4-Bis(ethylthio)-6-methylpyridin-3-yl]-N'-[2-(2chlorobenzo[b]thiophen-3-yl)-6-methylheptyl]urea 19% yield.

$^1$H NMR (300 MHz, CDCl$_3$) δ0.73, 0.75, 0.76, 0.78 (2d, 6H), 1.01–1.42 [c and 2t (1.22, 1.23, 1.24, 1.25, 1.27, 1.28), total 10H], 1.41 (h, 1H), 1.79 (c, 1H), 1.92 (c, 1H), 2,44 (s, 3H), 2.74 (c, 2H), 3.02 (q, 2H), 3.48 (c, 2H), 3.8 (c, 1H), 4.26 (b, 1H), 5.3 (s, 1H), 6.5 (s, 1H), 7.29 (m, 2H), 7.66 (m, 1H), 7.77 (c, 1H).

EXAMPLE 114

N-[2,4-Bis(ethylthio)-6-methylpyridin-3-yl]-N'-[2-(2chlorobenzo[b]thiophen-3-yl)-5-methylhexyl]urea 35% yield.

$^1$H NMR (300 MHz, CDCl$_3$) δ0.75–1.3 [c including 2d (0.77, 0.78, 0.79, 0.80, 6H), and 2t (1.22, 1.23, 1.24, 1.25, 1.27, 1.28, 6H), total 14H], 1.47 (h, 1H), 1.75–1.2 (c, 2H), 2.44 (s, 3H), 2.75 (c, 2H), 3.02 (q, 2H), 3.46 (c, 2H), 3.8 (c, 1H), 4.27 (b, 1H), 5.3 (s, 1H), 6.5 (s, 1H), 7.3 (m, 2H), 7.66 (m, 1H), 7.77 (c, 1H).

EXAMPLE 115

N-2,4-Bis(ethylthio)-6-methylpyridin-3-yl]-N'-[2-(5,6,7,8-tetrahydronaphth-1-yl)heptyl]urea 36% yield.

$^1$H NMR (300 MHz, CDCl$_3$) δ0.82 (t, 3H), 1.2 (c, 6H), 1.29, 1.31, 1.34 (2t, 6H), 1.45–1.82 (c, 6H), 2,46 (s, 3H), 2.7 (c, 4H), 2.83 (q, 2H), 3.03–3.28 (c including q (3.08), total 4H), 3.46 (p, 1H), 4.23 (b, 1H), 5.3 (s, 1H), 6.58 (s, 1H), 6.85, 6.88, 6.91 (2d, 2H), 6.98 (t, 1H).

EXAMPLE 116

N-[2,4-Bis(ethylthio)-6-methylpyridin-3-yl]-N'-[2-(3,5-dimethylphenyl)heptyl]urea 20% yield.

$^1$H NMR (300 MHz, CDCl$_3$) δ0.82 (t, 3H), 1.21 (c, 6H), 1.28, 1.30, 1.32, 1.35 (2t, 6H), 1.6 (c, 2H), 2.33 (s, 6H), 2.45 (s, 3H), 2.61 (c, 1H), 2.84 (q, 2H), 3.05–3.2 [c and q (3.1), total 3H], 3.56 (p, 1H), 4.2 (b, 1H), 5.3 (s, 1H), 6.59 (s, 1H), 6.67 (s, 2H), 6.78 (s, 1H).

EXAMPLE 117

N-[2,4-Bis(ethylthio)-6-methylpyridin-3-yl]-N'-[2-(2-chlorobenzo[b]thiophen-3-yl)heptyl]urea 51% yield.

$^1$H NMR (300 MHz, CDCl$_3$) δ0.79 (t, 3H), 1.04–1.32 [c including 2t (1.22, 1.23, 1.24, 1.25, 1.27, 1.28), total 12H], 1.81, (c, 1H), 1.94 (c, 1H), 2.44 (s, 3H), 2.76 (c, 2H), 3.02 (q, 2H), 3.48 (c, 2H), 3.8 (c, 1H), 4.27 (b, 1H), 5.3 (s, 1H), 6.5 (c, 1H), 7.3 (m, 2H), 7.66 (m, 1H), 7.78 (c, 1H).

EXAMPLE 118

N-[2,4-Bis(ethylthio)-6-methylpyridin-3-yl]-N'-[2-(3,5-dimethylphenyl)octyl]urea 19% yield.

$^1$H NMR (300 MHz, CDCl$_3$) δ0.83 (t, 3H), 1.2 (c, 8H), 1.27, 1.30, 1.32, 1.35 (2t, 6H), 1.45–1.72 (c, 2H), 2.22 (s, 6H), 2.45 (s, 3H), 2.6 (c, 1H), 2.84 (q, 2H), 3.05–3.2 [c and q (3.1), total 3H], 3.56 (h, 1H), 4.23 (b, 1H), 5.35 (s, 1H), 6.58 (s, 1H), 6.67 (s, 2H), 6.77 (s, 1H).

EXAMPLE 119

N-[2,4-Bis(ethylthio)-6-methylpyridin-3-yl]-N'-[2-(2,5-dimethyl-4-methoxyphenyl)heptyl]urea 50% yield.

$^1$H NMR (300 MHz, CDCl$_3$) δ0.82 (t, 3H), 1.2 (c, 6H), 1.26, 1.29, 1.31, 1.34 (2t, 6H), 1.44–1.72 (c, 2H), 2.09 (s, 3H), 2.18 (s, 3H), 2.46 (s, 3H), 2.82 (q, 2H), 3.96 (c, 1H), 3.01–3.2 [c including q (3.07), total 3H], 3.48 (p, 1H), 3.78 (s, 3H), 4.18 (b, 1H), 5.29 (s, 1H), 6.48 (s, 1H), 6.56 (s, 1H), 6.77 (s, 1H).

EXAMPLE 120

N-[2,4-Bis(methylthio)-6-methylpyridin-3-yl]-N'-[2-(5-methylbenzo[b]thiophen-3-yl)heptyl]urea 10% yield.

$^1$H NMR (300 MHz, CDCl$_3$) δ0.82 (t, 3H), 1.23 (c, 6H), 1.73 (c, 2H), 2.2 (s, 3H), 2.41 (s, 3H), 2.46 (s, 6H), 3.25 (p, 1H), 3.5 (t, 2H), 4.28 (b, 1H), 5.35 (s, 1H), 6.45 (s, 1H), 6.99 (s, 1H), 7.15 (d, 1H), 7.55 (s, 1H), 7.7 (d, 1H).

EXAMPLE 121

N-[2-(2-Chlorobenzo[b]thiophen-3-yl)-5-methylhexyl]-N'-(2,6-diisopropylphenyl)urea 43% yield.

$^1$H NMR (300 MHz, CDCl$_3$) δ0.72–1.31 (c, 20H), 1.46 (h, 1H), 1.78 (c, 1H), 1.82 (c, 1H), 3.06, (c, 2H), 3.44 (c, 2H), 3.76 (c, 1H), 4.01 (b, 1H), 5.52 (s, 1H), 7.06 (c, 2H), 7.26 (c, 3H), 7.64 (c, 1H), 7.71 (c, 1H).

EXAMPLE 122

N-(2,6-Diisopropylphenyl)-N'-[2-(5-methylbenzo[b]thiophen-3-yl)-5-methylhexyl]urea 44% yield.

$^1$H NMR (300 MHz, CDCl$_3$) δ0.76–1.3 [m, c including d (0.79, 0.81), total 21H], 1.46 (h, 1H), 1.68 (c, 2H), 2.45 (s, 3H), 3.08 (c) and 3.17 (m), (total 2H), 3.47 (c, 2H), 4.08 (b, 1H), 5.57 (s, 1H), 6.86 (s, 1H), 7.05 (s, 1H), 7.07 (s, 1H), 7.14 (d, 1H), 7.22 (d, 1H), 7.51 (s, 1H), 7.67 (d, 1H).

EXAMPLE 123

N-[2-(Benzo[b]thiophen-3-yl)heptyl]-N'-(2,6-diisopropylphenyl)urea

41% yield.

$^1$H NMR (300 MHz, CDCl$_3$) δ0.76–1.31 (c, 20H), 1.68 (c, 2H), 1.95 (c, 1H), 3.05 (c, 2H), 3.25 (p, 1H), 3.49 (c, 2H), 4.1 (b, 1H), 5.72 (s, 1H), 6.92 (s, 1H), 7.06 (s, 1H), 7.08 (s, 1H), 7.21–7.38 (c, 3H), 7.74 (m, 1H), 7.8 (m, 1H).

EXAMPLE 124

N-[2-(Benzo[b]thiophen-3-yl)-6-methylheptyl]-N'-(2,6-diisopropylphenyl)urea

58% yield.

$^1$H NMR (300 MHz, CDCl$_3$) δ0.74–1.48 [m, c including 2d (0.76, 0.77, 0.78, 0.80) total 22H], 1.67 (m, 2H), 1.8 (c, 1H), 3.07 (c, 2H), 3.25 (p, 1H), 3.48 (c, 2H), 4.1 (b, 1H), 5.68 (s, 1H), 6.92 (s, 1H), 7.06 (s, 1H), 7.08 (s, 1H), 7.2–7.4 (c, 3H), 7.74 (m, 1H), 7.8 (m, 1H).

EXAMPLE 125

N-[2-(2-Chlorobenzo[b]thiophen-3-yl)-6-methylheptyl]-N'-(2,6-diisopropylphenyl)urea 70% yield.

¹H NMR (300 MHz, CDCl₃) δ 0.7–1.3 !c and 2d (0,73, 0.75, 0.76, 0.78), total 22H], 1.4 (h, 1H), 1.73 (c, 1H), 1.91 (c, 1H), 3.06 (c, 2H), 3.44 (c, 2H), 3.76 (c, 1H), 4.02 (b, 1H), 5.54 (s, 1H), 7.06 (c, 2H), 7.2–7.32 (c, 3H), 7.64 (m, 1H), 7.71 (c, 1H).

EXAMPLE 126

N-(2,6-Diisopropylphenyl)-N'-[2-(5-Methylbenzo[b]thiophen-3-yl)-6,6,6-trifluorohexyl]urea 70% yield.

¹H NMR (300 MHz, CDCl₃) δ 0.8–1.3 (c, 12H), 1.51 (m, 2H), 1.78 (m, 2H), 2.0 (m, 2H), 2.46 (s, 3H), 3.07 (c, 2H), 3.25 (p, 1H), 3.48 (m, 2H), 4.11 (b, 1H), 5.6 (s, 1H), 6.92 (s, 1H), 7.07 (d, 2H), 7.16 (d, 1H), 7.24 (d, 1H), 7.52 (s, 1H), 7.69 (d, 1H).

EXAMPLE 127

N-[2-(2-Chlorobenzo[b]thiophen-3-yl)-6,6,6-trifluorohexyl]-N'-(2,6-diisopropylphenyl)urea 46% yield.

¹H NMR (300 MHz, CDCl₃) δ 0.78–1.27 (c, 12H), 1.42 (c, 2H), 1.85 (c, 1H), 2.02 (c, 3H), 3.08 (c, 2H), 3.47 (c, 2H), 3.79 (c, 1H), 4.08 (b, 1H), 5.58 (s, 1H), 7.07 (d, 2H) 7.2–7.35 (c, 3H), 7.7 (c, 2H).

EXAMPLE 128

N-(2,6-Diisopropylphenyl)-N'-[2-(naphth-2-yl)-6,6,6-trifluorohexyl]urea

67% yield.

¹H NMR (300 MHz, CDCl₃) δ 0.63–1.14 (c, 12H), 1.45 (m, 2H), 1.68–2.08 (c, 4H), 2.9 (c, 1H), 3.09 (c, 1H), 3.4 (c, 1H), 3.6 (c, 1H), 3.79 (c, 1H), 4.07 (b, 1H), 5.67 (s, 1H), 7.02 (d, 2H), 7.2 (m, 2H), 7.34 (t, 1H), 7.47 (m, 2H), 7.68 (d, 1H), 7.82 (m, 1H), 8.06 (c, 1H).

EXAMPLE 129

N-[7,7-Difluoro-2-(naphth-1-yl)heptyl]-N'-(2,6-diisopropylphenyl)urea

58% yield.

¹H NMR (300 MHz, CDCl₃) δ 0.63–1.46 (c, 16H), 1.57–1.9 (c, 4H), 2.92 (c, 1H), 3.08 (c, 1H), 3.39 (m, 1H), 3.59 (c, 1H), 3.75 (c, 1H), 4.03 (b, 1H), 5.57 (s, 1H), 5.48 5.67, 5.86 (3t, total 1H), 7.0 (d, 1H), 7.18 (t, 2H), 7.32 (t, 1H), 7.44 (m, 2H), 7.65 (d, 1H), 7.8 (m, 1H), 8.05 (m, 1H).

EXAMPLE 130

N-[7,7-difluoro-2-(2-chlorobenzo[b]thiophen-3-yl)heptyl]-N'-(2,6-diisopropylphenyl)urea 73% yield.

¹H NMR (300 MHz, CDCl₃) δ 0.73–1.5 (c, 16H), 1.56–1.85 (c, 3H), 1.96 (c, 1H), 3.07 (c, 2H), 3.47 (c, 2H), 3.77 (c, 1H), 4.05 (b, 1H), 5.59 (s, 1H), 5.50, 5.69, 5.88 (3t, total 1H), 7.06 (d, 2H), 7.2–7.35 (c, 3H), 7.62–7.77 (c, 2H).

EXAMPLE 131

N-[2-(5-Chlorobenzo[b]thiophen-3-yl)heptyl]-N'-(2,6-diisopropylphenyl)urea

59% yield.

¹H NMR (300 MHz, CDCl₃) δ 0.77–1.46 (c, 21H), 1.65 (m, 2H), 3.01–3.24 (m, 3H), 3.46 (m, 2H), 4.04 (b, 1H), 5.6 (s, 1H), 7.02 (s, 1H), 7.08 (c, 2H), 7.2 (m, 2H), 7.71 (m, 2H).

EXAMPLE 132

N-[2-(2-Chlorobenzo[b]thiophen-3-yl)heptyl]-N'-(2,6-diisopropylphenyl)urea

60% yield.

¹H NMR (300 MHz, CDCl₃) δ 0.74–1.42 (c, 21H), 1.75 (c, 1H), 1.92 (c, 1H), 3.07 (c, 2H), 3.45 (c, 2H), 3.76 (c, 1H), 4.02 (b, 1H), 5.74 (s, 1H), 7.06 (c, 2H), 7.2–7.34 (m, 3H), 7.65 (m, 1H), 7.7 (c, 1H).

EXAMPLE 133

N-[2-(5-Chlorobenzo[b]thiophen-3-yl)-6,6,6-trifluorohexyl]-N'-(2,6-diisopropylphenyl)urea 72% yield.

¹H NMR (300 MHz, CDCl₃) δ 0.82–1.32 (c, 12H), 1.5 (m, 2H), 1.76 (c, 2H), 2.0 (c, 2H), 3.07 (c, 2H), 3.23 (p, 1H), 3.48 (c, 2H), 4.11 (b, 1H), 5.68 (s, 1H), 7.07, 7.09 (d and s, 3H), 7.21–7.34 (m, 2H), 7.72, 7.75 (d and s, 2H).

EXAMPLE 134

N-(2,6-(Diisopropylphenyl)-N'-[2-(5-methylbenzo[b]thiophen-3-yl)heptyl]urea

50% yield.

¹H NMR (300 MHz, CDCl₃) δ 0.76–1.32 (c, 21H), 1.67 (c, 2H), 2.45 (s, 3H), 3.08 (c, 2H), 3.2 (p, 1H), 3.47 (t, 2H), 4.06 (b, 1H), 5.6 (s, 1H), 6.86 (s, 1H), 7.07 (d, 2H), 7.14 (d, 1H), 7.22 (d, 1H), 7.52 (s, 1H), 7.67 (d, 1H).

EXAMPLE 135

N-[2-(5-Chlorobenzo[b]thiophen-3-yl)-6-methylheptyl]-N'-(2,6-diisopropylphenyl)urea 49% yield.

¹H NMR (300 MHz, CDCl₃) δ 0.75–1.8 [c including 2d (0.76, 0.78, 0.79, 0.80), total 23H), 2.26 (m, 2H), 3.07 (p, 2H), 3.18 (p, 1H), 3.47 (c, 2H), 4.06 (b, 1H), 5.65 (s, 1H), 7.03 (s, 1H), 7.08 (c, 2H), 7.2–7.3 (m, 2H), 7.71 (m, 2H).

EXAMPLE 136

N-(2,6-(Diisopropylphenyl)-N'-[2-(2,5-dimethylphenyl)-6,6,6-trifluorohexyl]urea

37% yield.

¹H NMR (300 MHz, CDCl₃) δ 0.9–1.76 (c, 16H), 1.98 (m, 2H), 2.08 (s, 3H), 2.19 (s, 3H), 2.95–3.21 (c, 4H), 3.52 (p, 1H), 3.97 (b, 1H), 5.6 (b, 1H), 6.74 (s, 1H), 6.83 (d, 1H), 6.9 (d, 1H), 7.11 (d, 2H), 7.28 (t, 1H).

EXAMPLE 137

N-[7,7-Difluoro-2-(2,5-dimethylphenyl)heptyl]-N'-(2,6-diisopropylphenyl)urea

65% yield.

¹H NMR (300 MHz, CDCl₃) δ 0.92–1.82 (c, 20H), 2.06 (s, 3H), 2.18 (s, 3H), 2.98 (c, 1H), 3.12 (c, 3H), 3.51 (p, 1H), 3.95 (b, 1H), 5.61 (s, 1H), 5.52, 5.71, 5.9 (3t, total 1H), 6.74 (s, 1H), 6.81 (d, 1H), 6.89 (d, 1H), 7.1 (d, 2H), 7.27 (t, 1H).

EXAMPLE 138

N-(2,6-Diisopropylphenyl)-N'-[2-(napth-1-yl)heptyl]urea

61% yield.

$^1$H NMR (300 MHz, CDCl$_3$) δ0.78 (t, 3H), 0.9–1.3 (m and c, 18H), 1.72 (c, 2H), 2.85–3.16 (c, 2H), 3.41 (m, 1H), 3.58 (c, 1H), 3.72 (c, 1H), 4.02 (b, 1H), 5.49 (s, 1H), 7.01 (d, 2H), 7.18 (m, 2H), 7.31 (t, 1H), 7.44 (m, 2H), 7.65 (d, 1H), 7.8 (m, 1H), 8.07 (m, 1H).

EXAMPLE 139

N-(2,6-Diisopropylphenyl)-N'-[6-methyl-2-(napth-1-yl)heptyl]urea

59% yield.

$^1$H NMR (300 MHz, CDCl$_3$) δ0.74 (t, 6H), 0.91–1.29 (m and c, 18H), 1.4 (h, 1H), 1.7 (c, 2H), 2.84–3.16 (c, 2H), 3.41 (m, 1H), 3.51–3.8 (c, 2H), 4.02 (c, 1H), 5.51 (s, 1H), 7.0 (d, 2H), 7.19 (m, 2H), 7.31 (t, 1H), 7.44 (m, 2H), 7.66 (d, 1H), 8.07 (m, 1H).

I claim:

1. A compound of the formula

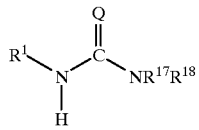

I wherein Q is oxygen or sulfur

R$^{17}$ is —(CH$_2$)$_n$—CR$^{19}$R$^{20}$)$_z$(CH$_2$)$_r$—AR  XXXVIII wherein n is 1;

z is 1;

and r is 0;

R$^{19}$ and R$^{20}$ are independently selected from hydrogen, optionally halogenated (C$_4$–C$_{12}$) alkyl, optionally substituted aryl-(C$_1$–C$_5$)alkyl, (C$_3$–C$_8$)cycloalkyl-(C$_1$–C$_5$) alkyl and Ar; or R$^{19}$ and R$^{20}$ and the carbon to which they are attached form a (C$_4$–C$_7$) cycloalkyl ring or a benzene-fused (C$_5$–C$_7$) cycloalkyl or -heteroalkyl ring; with the proviso that R$^{19}$ and R$^{20}$ cannot both be hydrogen;

Ar is selected from the group consisting of

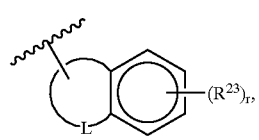

XXX

XXXI

XXXII

-continued

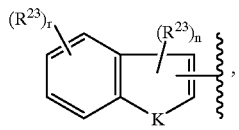

XXXIII

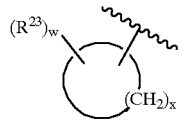

XXXIV and

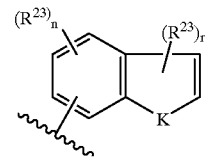

XXXV wherein U is J, a direct bond, —CH=CH— or —CH$_2$CH$_2$—;

z, n and r are as defined above; x is an integer from 3 to 10 and w is 0 or an integer from 1 to x−1;

R$^{21}$, R$^{22}$ and each R$^{23}$ is independently selected from the group consisting of optionally halogenated (C$_1$–C$_6$) alkyl, optionally halogenated (C$_1$–C$_6$)alkoxy, optionally halogenated (C$_1$–C$_6$)alkylthio, phenyl and halogen; wherein the alkyl groups in said alkyl, alkoxy and althylthio groups may be straight chained or if comprising three or more carbons may be branched, cyclic or a combination of cyclic and branched or straight chain moieties;

or R$^{21}$ and R$^{22}$ together form a group of the formula

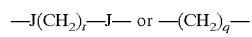

wherein J is oxygen or sulfur;

t is an integer from 1 to 3;

and q is an integer from 3 to 5;

K is J— or —CH=CH—;

L is —(CH$_2$)$_u$ or —(CH$_2$)$_v$J—;

wherein J is as defined above;

u is a n integer 3 to 5;

and v is 2, 3 or 4;

R$^{18}$ is hydrogen,

R$^1$ is

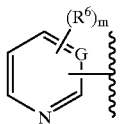

wherein m is 0 or an integer from 1 to 4;

y is 0 or 1;

Each R$^6$ is independently selected from the group consisting of halogen, optionally halogenated (C$_1$–C$_6$) alkyl, optionally halogenated (C$_1$–C$_6$)alkoxy, optionally halogenated (C$_1$–C$_6$)alkylthio, (C$_5$–C$_7$) cycloalkylthio, phenyl (C$_1$–C$_6$)alkylthio, substituted phenylthio, heteroarylthio, heteroaryloxy, (C$_1$–C$^6$)

alkylsulfinyl, $(C_1-C_6)$alkylsulfonyl, $(C_5-C_7)$ cycloalkylsulfinyl, $(C_5-C_7)$cycloalkylsulfonyl, phenyl $(C_1-C_6)$alkylsulfinyl, phenyl$(C_1-C_6)$alkylsulfonyl, substituted phenylsulfinyl, substituted phenylsulfonyl, heteroarylsulfinyl, heteroarylsulfonyl, and $NR^{10}R^{11}$, wherein $R^{10}$ and $R^{11}$ are the same or different and are selected from the group consisting of hydrogen, $(C_1-C_6)$alkyl, phenyl, substituted phenyl, $(C_1-C_6)$acyl, aroyl, and substituted aroyl, wherein said substituted phenyl and substituted aroyl groups are substituted with one or more substituents independently selected from the group consisting of $(C_1-C_6)$ alkyl, $(C_1-C_6)$ alkoxy, $(C_1-C_6)$ alkylthio, halogen and trifluoromethyl, or $R^{10}$ and $R^{11}$, together with the nitrogen to which they are attached, form a piperidine, pyrrolidine or morpholine ring; and G is carbon and the nitrogen may be oxidized; or a pharmaceutically acceptable salt of said compound.

2. The compound according to claim 1 wherein $R^1$ is

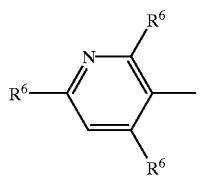

XXVIA and each $R^6$ is independently selected from the group consisting of $(C_1-C_8)$alkyl, and $(C_1-C_8)$alkylthio, $R^{17}$ is selected from the group consisting of benzenefused $(C_5-C_8)$ cycloalkyl and optionally substituted $(C_1-C_8)$ alkyl wherein said substituents are selected from the group consisting of phenyl, biphenyl, fluorenyl, benzo [b]thiophenyl, naphthyl, halogen and $(C_3-C_{12})$ cycloalkyl wherein said phenyl, naphthyl, cycloalkyl, biphenyl, fluorenyl and benzo[b]thiophenyl groups are optionally substituted with substituents selected from the group consisting of optionally halogenated $(C_1-C_6)$ alkoxy, optionally halogenated $(C_1-C_6)$alkyl, optionally halogenated $(C_1-C_6)$alkylthio and halogen and $R^{18}$ is hydrogen.

3. A compound according to claim 1, said compound being selected from the group consisting of:

N-[2,4-Bis(methylthio)-6-methylpyridin-3-yl]-N'-[2,2-diphenylethyl]urea;

N-[4,6-Bis(methylthio)-6-methylpyridin-3-yl]-N'-[(1-phenylcyclopentyl)methyl]urea;

N-[4,6-Bis(methylthio)-6-methylpyridin-3-yl]-N'-[{1-(4-methylphenyl)cyclopentyl)methyl}urea;

N-[2,4-Bis(methylthio)-6-methylpyridin-3-yl]-N'-[(1-phenylcyclohexyl)methyl]urea;

N-[2,4-Bis(methylthio)-6-methylpyridin-3-yl]-N'-[{1-(4-methylphenyl)cyclohexyl}methyl]urea;

N-[2,4-Bis(methylthio)-6-methylpyridin-3-yl]-N'-[(2-ethyl-2-phenyl)butyl]urea;

N-[2,4-Bis(isopropylthio)-6-methylpyridin-3-yl]-N'-[(2-ethyl-2-phenyl)butyl]urea;

N-[2,4-Bis(methylthio)-6-methylpyridin-3-yl]-N'-[(2-ethyl-2-{2-methylphenyl})butyl]urea;

N-[2,4-Bis(methylthio)-6-methylpyridin-3-yl]-N'-[(2-phenyl-2-propyl)penty]urea;

N-[2,4-Bis(methylthio)-6-methylpyridin-3-yl]-N'-[(2-{2-methylphenyl}-2-propyl)pentyl]urea;

N-[2,4-Bis(methylthio)-6-methylpyridin-3-yl]-N'-[(2-{2-methylphenyl}-2-butyl)hexyl]urea;

N-[2,4-Bis(methylthio)-6-methylpyridin-3-yl]-N'-[(2-{2,5-dimethoxyphenyl}-2-propyl)pentyl]urea;

N-[2,4-Bis(methylthio)-6-methylpyridin-3-yl]-N'-[(2-{2,3-dimethoxyphenyl}-2-propyl)pentyl]urea;

N-[2,4-Bis(methylthio)-6-methylpyridin-3-yl]-N'-[(2-{2,5-dimethylphenyl}-2-propyl)pentyl]urea;

N-[2,4-Bis(methylthio)-6-methylpyridin-3-yl]-N'-[2-(2-methylphenyl)hexyl]urea;

N-[2,4-Bis(methylthio)-6-methylpyridin-3-yl]-N'-[2-(4-methylphenyl)heptyl]urea;

N-[2,4-Bis(methylthio)-6-methylpyridin-3-yl]-N'-[2-(3-methylphenyl)heptyl]urea;

N-[2-(4-Bis(methylthio)-6-methylpyridin-3-yl-]-N'-[2-(2,5-dimethylphenyl)hexyl]urea;

N-[2,4-Bis(methylthio)-6-methylpyridin-3-yl}-N'-{2-(2,5-dimethylphenyl)heptyl]urea;

N-[2,4-Bis(methylthio)-6-methylpyridin-3-yl-}-N'-{2-(2,4-dimethylphenyl)hexyl]urea;

N-[2,4-Bis(methylthio)-6-methylpyridin-3-yl}-N'-{2-(3-methylphenyl)hexyl]urea;

N-[2,4-Bis(methylthio)-6-methylpyridin-3-yl}-N'-{2-(2,4-dimethylphenyl)heptyl]urea;

N-[2,4-Bis(methylthio)-6-methylpyridin-3-yl}-N'-{2-(naphth-1-yl)heptyl]urea;

N-[2,4-Bis(methylthio)-6-methylpyridin-3-yl}-N'-{2-(naphth-2-yl)hexyl]urea;

N-[2,4-Bis(methylthio)-6-methylpyridin-3-yl}-N'-{2-(naphth-1-yl)hexyl]urea

N-[2,4-Bis(methylthio)-6-methylpyridin-3-yl]-N'-[2-(2,3-dimethoxyphenyl)heptyl]-urea;

N-[2,4-Bis(methylthio)-6-methylpyridin-3-yl]-N'-[2-(3-methylphenyl)octyl]urea;

N-[2,4-Bis (methyl)-6-methylpyridin-3-yl]-N'-[2-(3,4,5-trimethoxyphenyl)heptyl]urea;

N-[2,4-Bis(methylthio)-6-methylpyridin-3-yl]-N'-[2,5-dimethyl-4-methoxyphenyl)heptyl]urea;

N-[2,4-Bis(methylthio)-6-methylpyridin-3-yl]-N'-[2-(2,5-dimethoxyphenyl)heptyl]urea;

N-[2,4-Bis(methylthio)-6-methylpyridin-3-yl]-N'-(2-(3,5-dimethoxyphenyl)heptyl]urea;

N-[2,4-Bis(methylthio)-6-methylpyridin-3-yl]-N'-(2-(2,5-dimethoxyphenyl)octyl]urea;

N-[2,4-Bis(methylthio)-6-methylpyridin-3-yl]-N'-2-[2-(3-methylphenyl)-6,6,6-trifluorohexyl]urea;

N-[2,4-Bis(methylthio)-6-methylpyridin-3-yl]-N'-{2,-(5-chlorobenzo[b]thiophen-3-yl)heptyl}urea N-[2,4-Bis(methylthio)-6-methylpyridin-3-yl]-N'-[2-(3,5-dimethylphenyl)heptyl]urea;

N-[2,4-Bis(methylthio)-6-methylpyridin-3-yl]-N'-[2-(2,5-dimethylphenyl)octyl]urea;

N-[2,4-Bis(methylthio)-6-methylpyridin-3-yl]-N'-[5-methyl-2-{3-methylphenyl}hexyl]urea;

N-[2,4-Bis(methylthio)-6-methylpyridin-3-yl]-N'-[(2-{2,5-dimethylphenyl}-4-phenylbutyl]urea; and N-[2,4-Bis(methylthio)-6-methylpyridin-3-yl]-N'-[2-(2,5-dimethylphenyl)-5-phenylpentyl]urea.

4. A pharmaceutical composition comprising an ACAT inhibiting effective amount of a compound according to claim 1 and a pharmaceutically acceptable diluent or carrier.

5. A method of inhibiting ACAT in a human or animal comprising administering to said human or animal an ACAT inhibiting amount of a compound according to claim 1.

* * * * *